(12) United States Patent
Aviram et al.

(10) Patent No.: US 6,362,236 B1
(45) Date of Patent: Mar. 26, 2002

(54) INHIBITION OF LIPOPROTEIN OXIDATION

(75) Inventors: Michael Aviram, Halfa (IL); Charles Larry Bisgaier; Roger Schofield Newton, both of Ann Arbor, MI (US); Mira Rosenblat, Halfa (IL)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/485,250

(22) PCT Filed: Nov. 4, 1998

(86) PCT No.: PCT/US98/23483

§ 371 Date: Feb. 7, 2000

§ 102(e) Date: Feb. 7, 2000

(87) PCT Pub. No.: WO99/26583

PCT Pub. Date: Jun. 3, 1999

Related U.S. Application Data

(60) Provisional application No. 60/066,888, filed on Nov. 25, 1997.

(51) Int. Cl.[7] .............. A61K 31/40; A61K 31/405; A61K 31/192; A61P 39/06; A61P 39/04

(52) U.S. Cl. ................ 514/824; 514/428; 514/419; 514/570

(58) Field of Search ................. 514/824, 428, 514/419, 570; 424/451, 464, 468

(56) References Cited

U.S. PATENT DOCUMENTS 5,385,929 A    1/1995  Bjorge et al. ............... 514/422

OTHER PUBLICATIONS

Husein, et al., Atherosclerosis, "Reduced Susceptibility of Low Density Lipoprotein to Lipid Peroxidation After Fluvastatin Thereapy is Associated with the Hypocholesterolemic Effect of the Drug and its Binding to the LDL", 1997, vol. 123:1, pp. 11–18, Chemical Abstracts.

Aviram, M., EUR J. Clin. Chem. Clin. Biochem., "Interaction of Oxidized Low Density Lipoprotein with Macrophages in Atherosclerosis, and the Antiatherogenicity of Antioxidants", 1996, vol. 34, pp. 599–608 PCT International Search Report, PCT/US98/23483.

Primary Examiner—Edward J. Webman
Assistant Examiner—Helen Nguyen
(74) Attorney, Agent, or Firm—Charles W. Ashbrook

(57) ABSTRACT

Hydroxylated derivatives of cholesterol lowering agents inhibit the oxidation of lipoproteins, and are thus useful for preventing the progression of atherogenesis and resultant vascular diseases, including heart attacks.

7 Claims, 24 Drawing Sheets

EFFECT OF ATORVASTATIN METABOLITE ON MEMBRANE LIPID PEROXIDATION

Figure 3A:
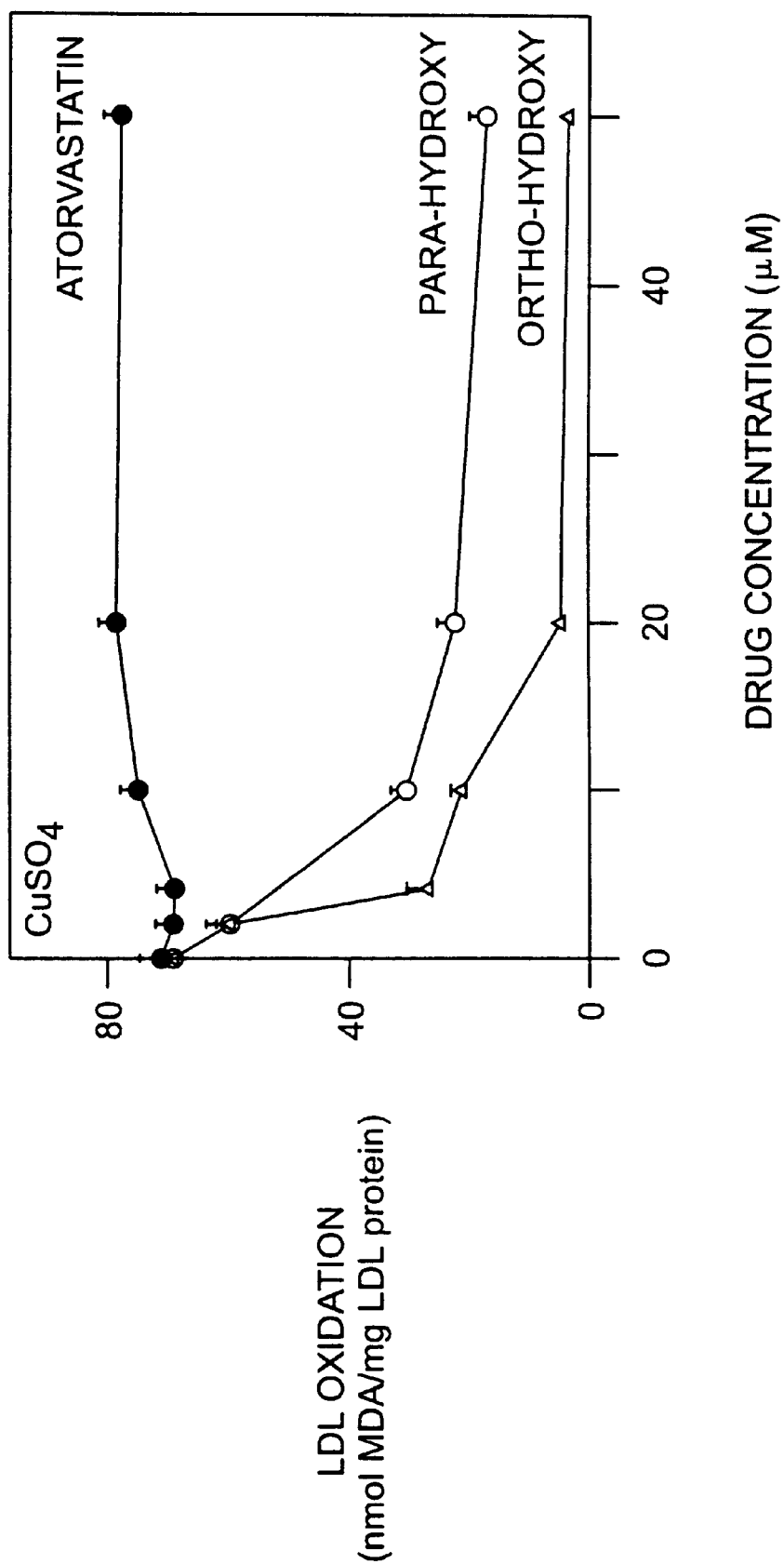

*$P<0.01$.
**$P<0.001$.
VALUES ARE MEAN ± SD. CONTROL LOOH=1300 μM: 48H INCUBATION AT 37°C.

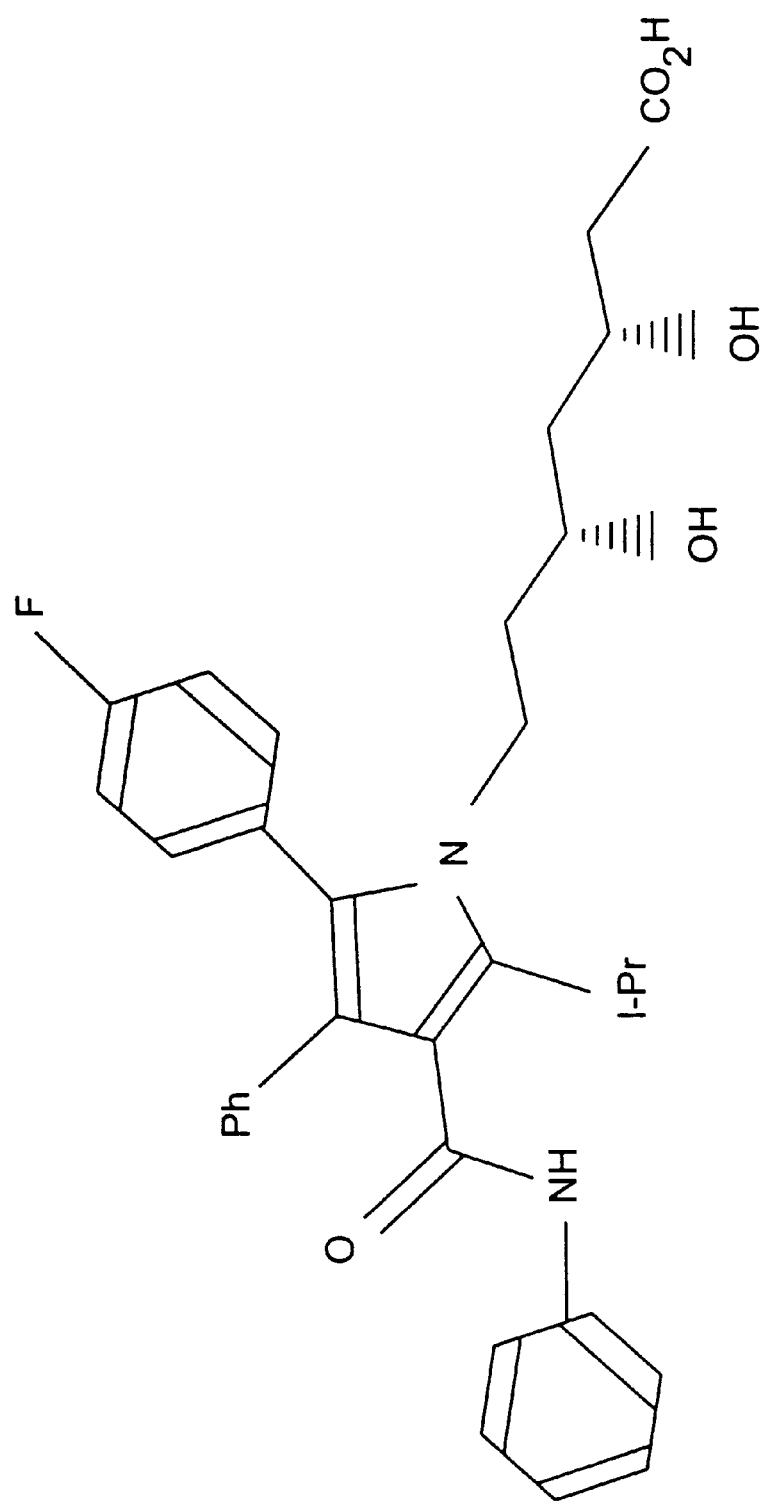
FIG-1a ATORVASTATIN

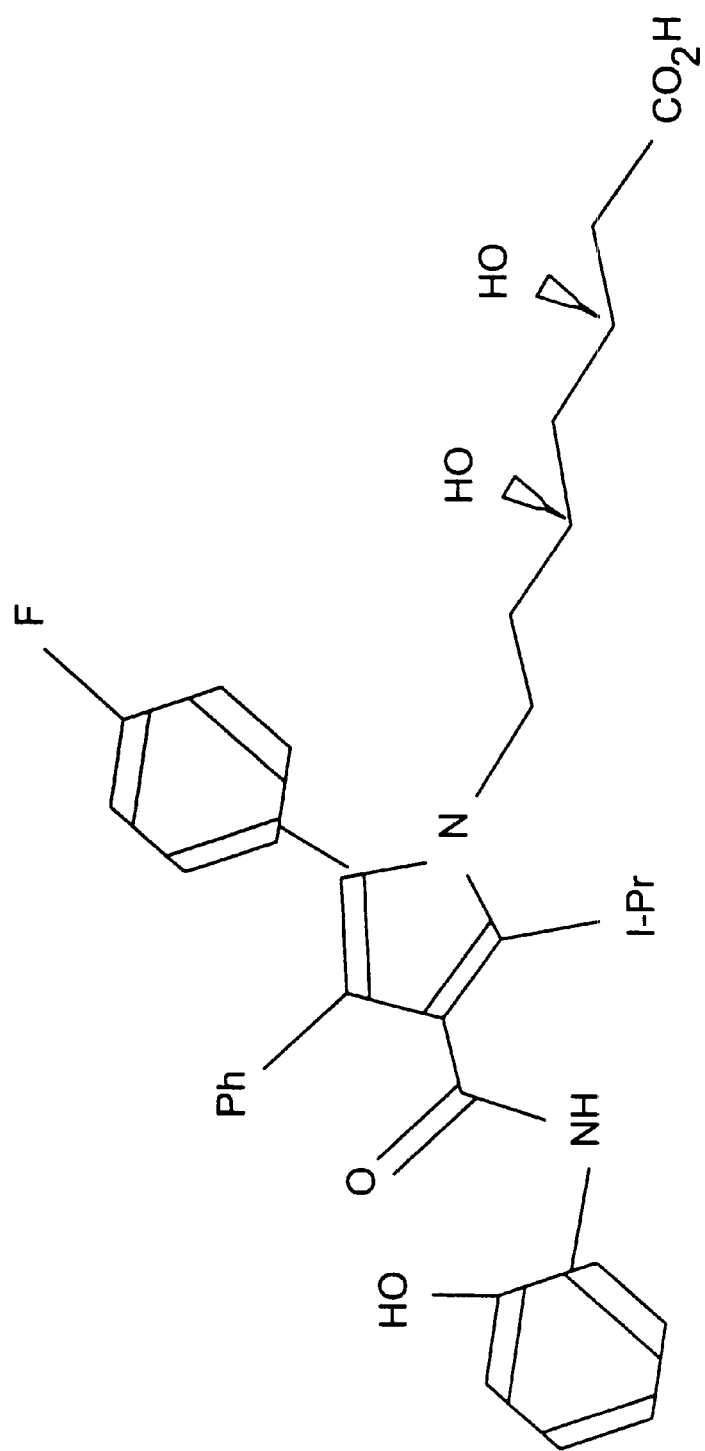
FIG-1b  ORTHO-HYDROXY METABOLITE

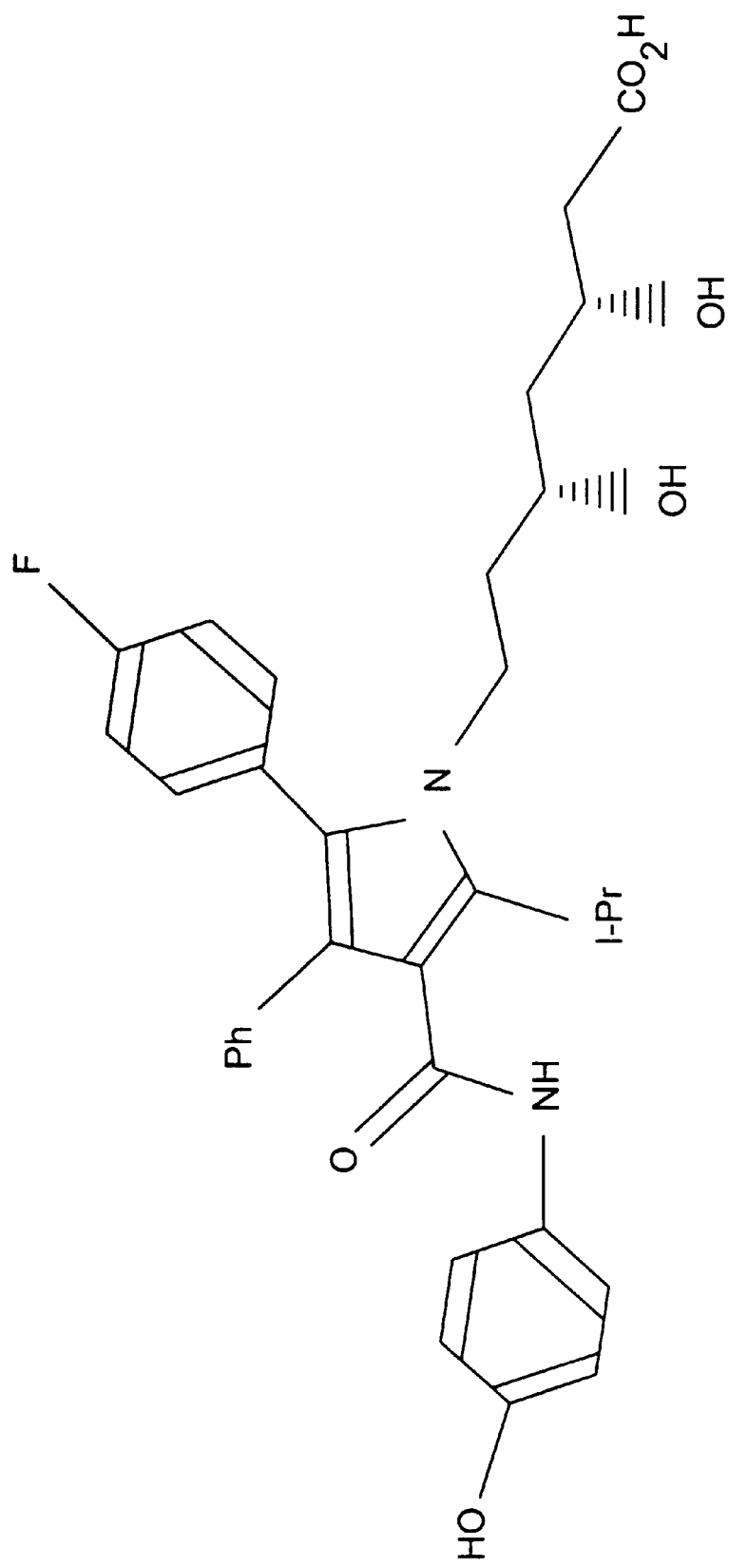
FIG-1c PARA-HYDROXY METABOLITE

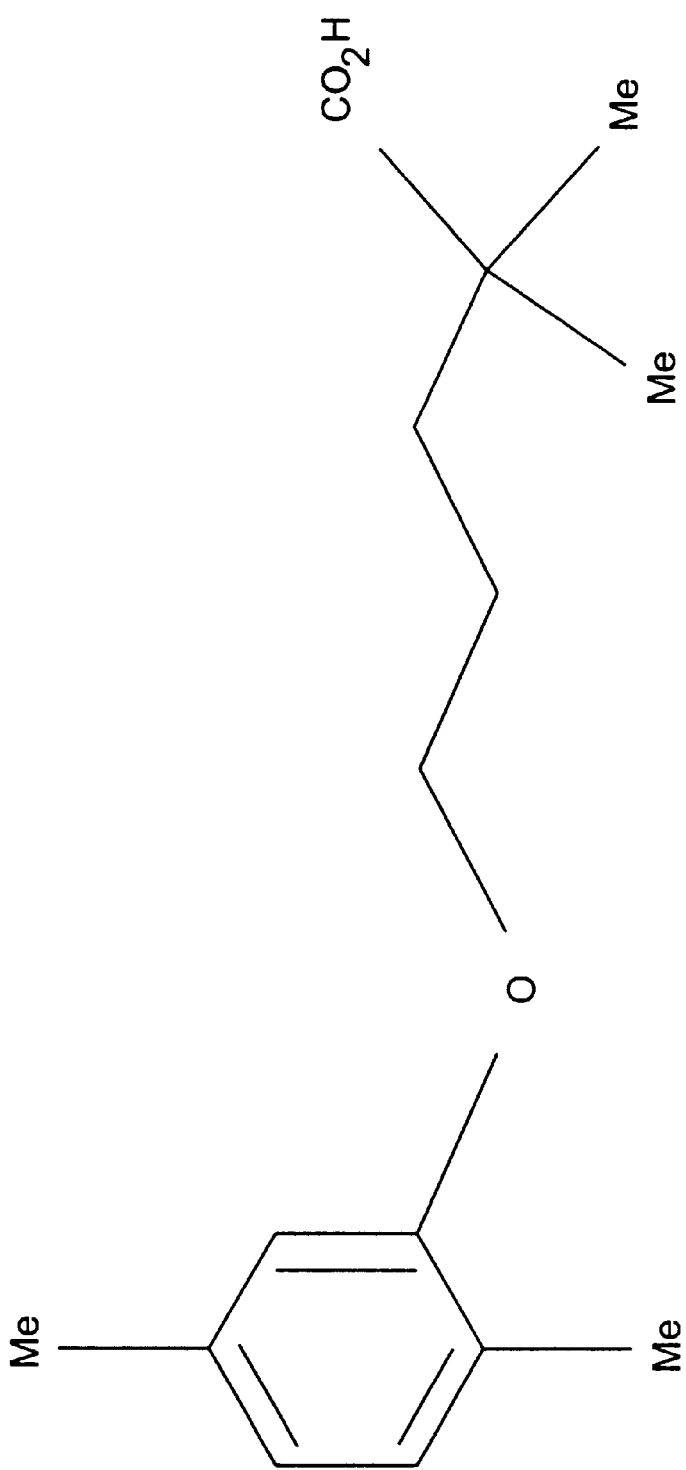
FIG-2a GEMFIBROZIL

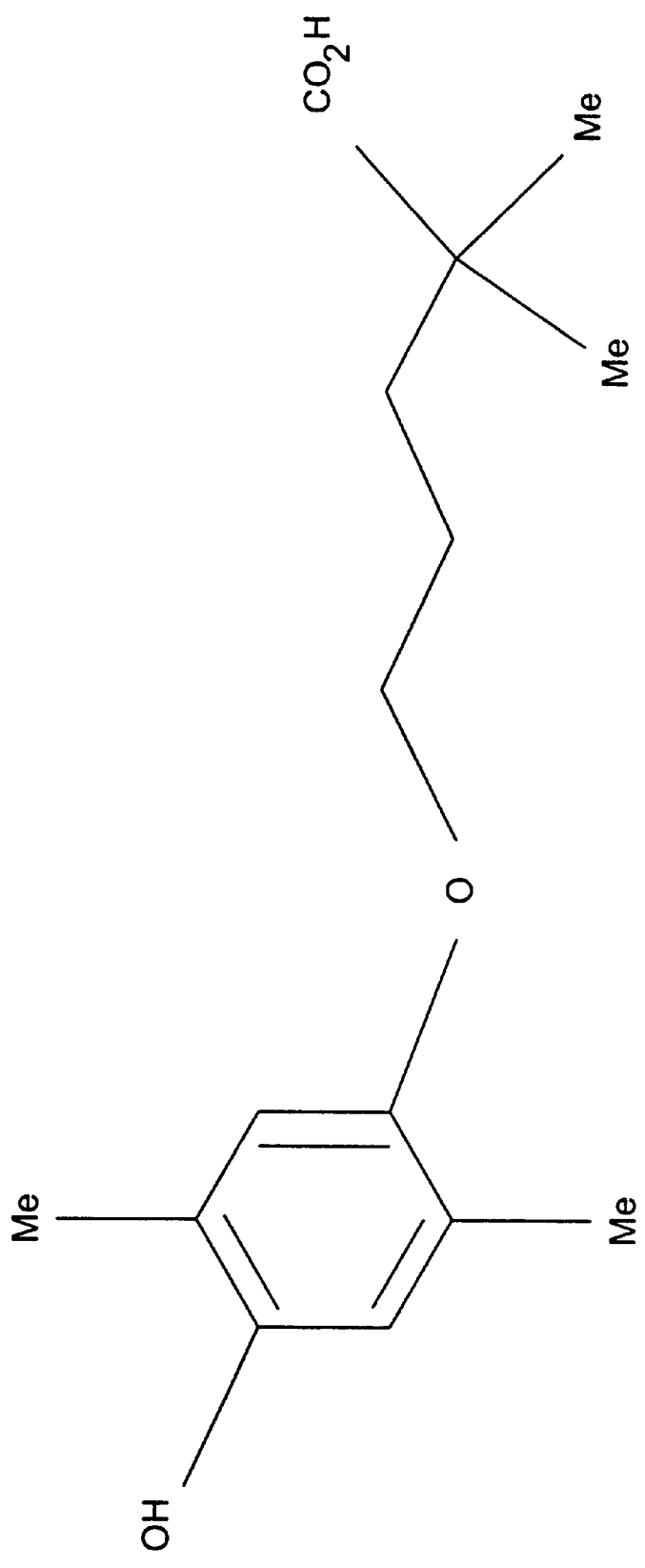
FIG-2b METABOLITE I

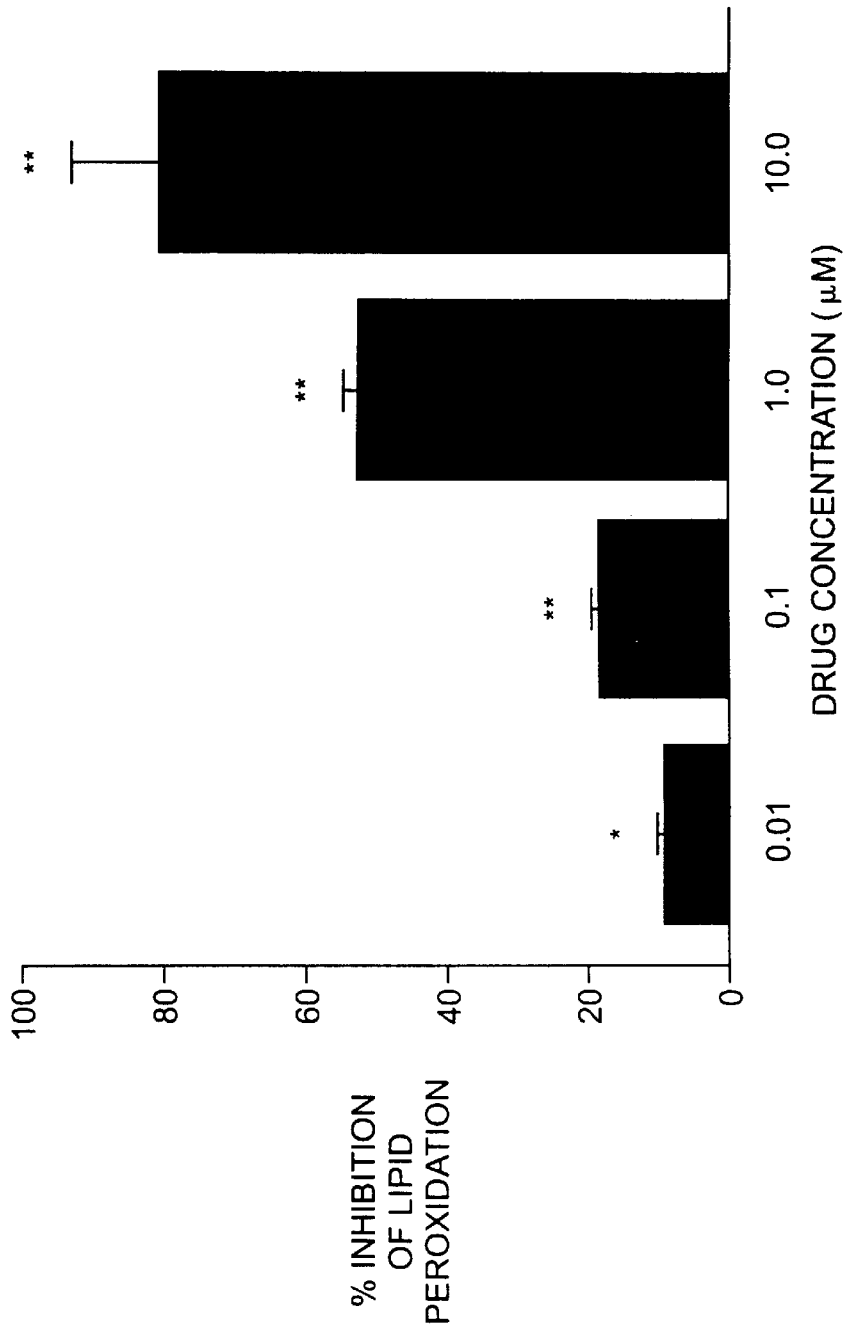

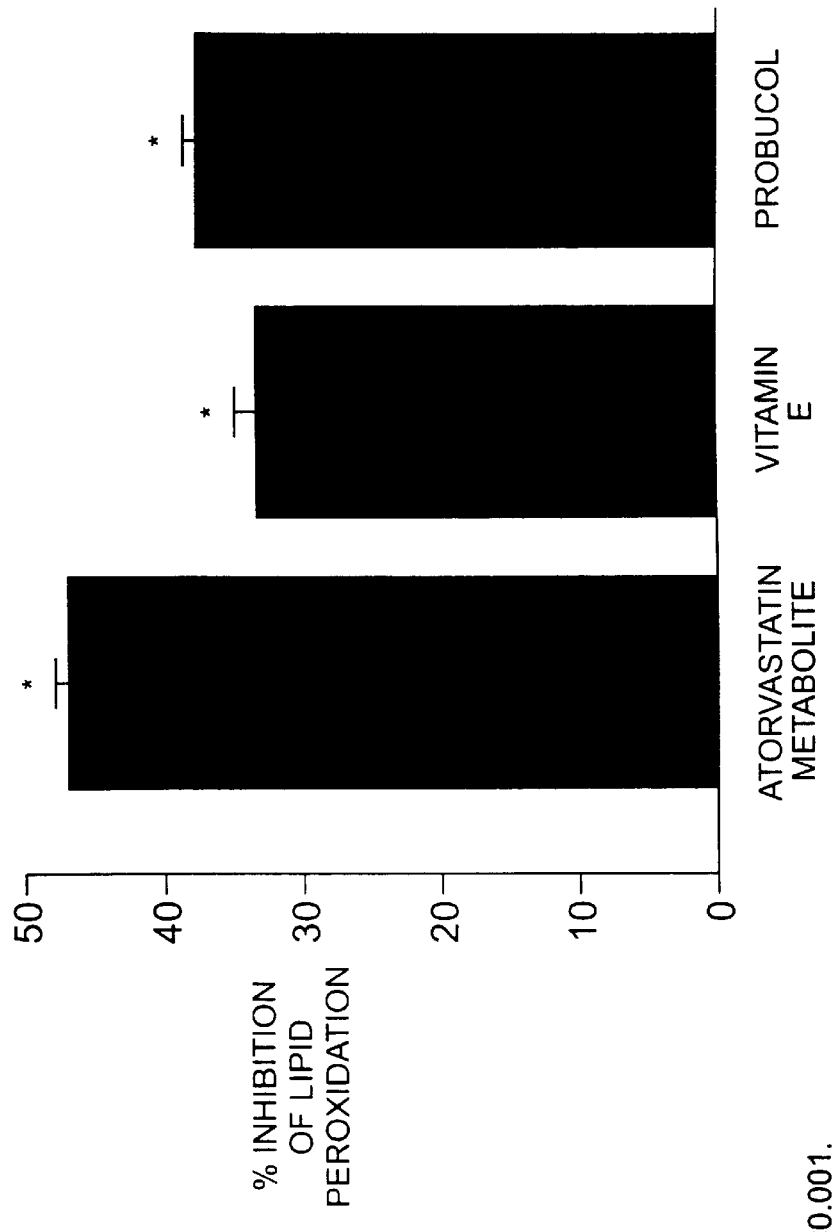

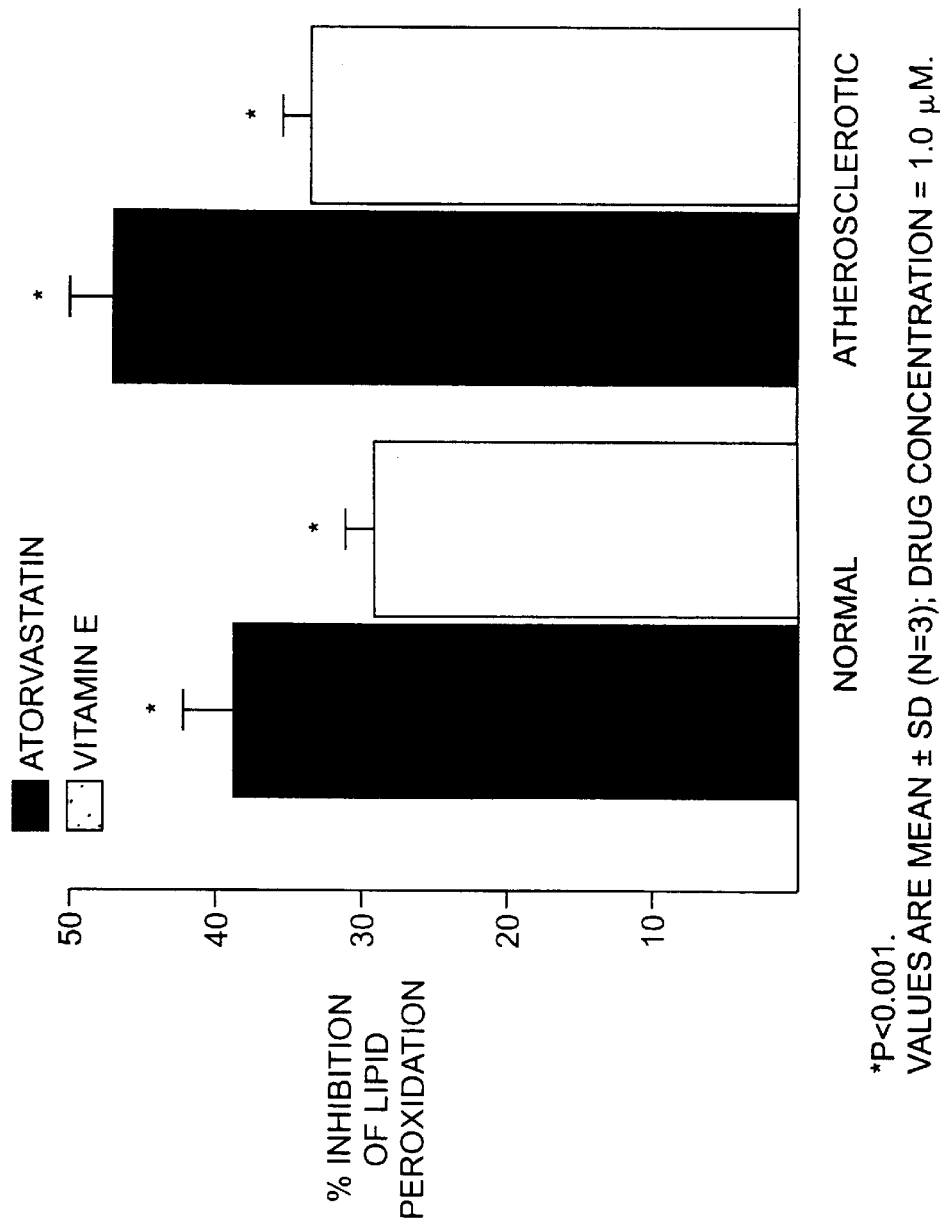

INHIBITION OF LIPOPROTEIN OXIDATION

This application is a 371 of PCT/U.S. 98/23483 filed Nov. 4, 1998 which claim benefit of Provisional No. 60/066,888 filed Nov. 25, 1997.

FIELD OF THE INVENTION

This invention relates to a method for inhibiting the oxidation of lipoproteins, thereby slowing or stopping atherogenesis. The method entails the use of hydroxylated derivatives of known cholesterol lowering agents.

BACKGROUND OF THE INVENTION

Atherosclerotic cardiovascular diseases and related conditions and disease events associated with hyperlipidemia are major causes of disability and death. It is now well recognized that lowering certain forms of cholesterol, both in healthy mammals as well as in individuals already experiencing states of hyperlipidemia, can dramatically reduce heart attacks, vascular disease, and other diseases associated with atherosclerotic conditions.

Hyperlipidemia is a condition which is characterized by an abnormal increase in serum lipids, such as cholesterol, triglycerides, and phospholipids. These lipids do not circulate freely in solution in plasma, but are bound to proteins and transported as macromolecular complexes called lipoproteins. There are five classifications of lipoproteins based on their degree of density: chylomicrons, very low density lipoproteins (VLDL), low density lipoproteins (LDL), intermediate density lipoproteins (IDL), and high density lipoproteins (HDL).

One form of hyperlipidemia is hypercholesterolemia, characterized by the existence of elevated LDL cholesterol levels. The initial treatment for hypercholesterolemia is often to modify the diet to one low in fat and cholesterol, coupled with appropriate physical exercise, followed by drug therapy when LDL-lowering goals are not met by diet and exercise alone. LDL is commonly known as the "bad" cholesterol, while HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD).

While LDL cholesterol is recognized as bad, and most cholesterol-lowering agents operate by lowering the plasma concentration of the LDL form, there is another key process in the early stages of atherogenesis, that being oxidation of LDL. Oxidation of VLDL and HDL also occurs, which also contributes to atherogenesis. Oxidation leads to increased intracellular calcium, lowered energy production, activation of cytokines, membrane damage, all resulting in apoptosis, necrosis, and ultimately cell death.

Oxidation typically begins when a reactive radical abstracts a hydrogen atom from a polyunsaturated fatty acid on the LDL particle. Lipid peroxyl and alkoxyl radicals are formed, which in turn can initiate oxidation in neighboring fatty acids, resulting in propogation of lipid peroxidation. These oxidized forms of lipoproteins are absorbed by macrophages more rapidly than the native lipoproteins, and this results in macrophage cholesterol accumulation, and subsequent foam cell formation and inhibition of the motility of tissue macrophages and endothelial cells. This cascade of events results in vascular dysfunction and formation and activation of atherosclerotic lesions.

We have now discovered that certain hydroxy-substituted derivatives of commonly employed cholesterol lowering agents are effective antioxidants for lipoproteins. Additionally, these compounds are useful for free radical scavenging and metal ion chelation, which also are mechanisms by which lipoproteins are oxidized.

SUMMARY OF THE INVENTION

This invention provides a method for inhibiting oxidation of lipoproteins in a mammal comprising administering an antioxidant effective amount of a hydroxylated cholesterol lowering agent. The invention also provides a method for scavenging free radicals in a mammal comprising administering a free radical scavenging amount of a hydroxylated cholesterol-lowering agent. The invention also provides a method for inhibiting metal ion chelation by lipoproteins comprising administering an effective amount of a hydroxylated cholesterol lowering agent.

In a preferred embodiment, the methods are practiced utilizing a hydroxylated form of a statin, especially atorvastatin, which compounds are described in U.S. Pat. No. 5,385,929, which is incorporated herein by reference.

In another preferred embodiment, the methods are practiced utilizing a hydroxylated gemfibrozil, e.g., a compound of the formula

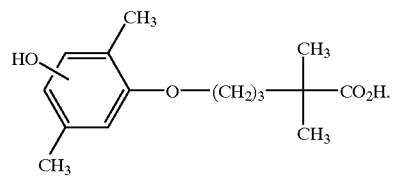

in another embodiment, a hydroxylated fluvastatin is employed, e.g., compounds of the formula

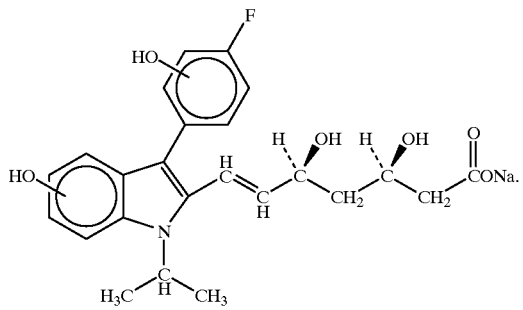

In another embodiment, a hydroxylated cerivastatin is employed, especially a compound of the formula

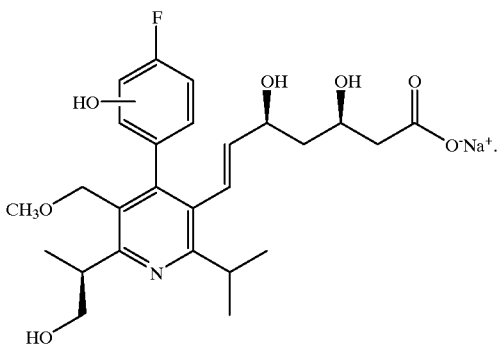

In another preferred embodiment, hydroxylated derivatives of lovastatin are employed, e.g., compounds of the formulas

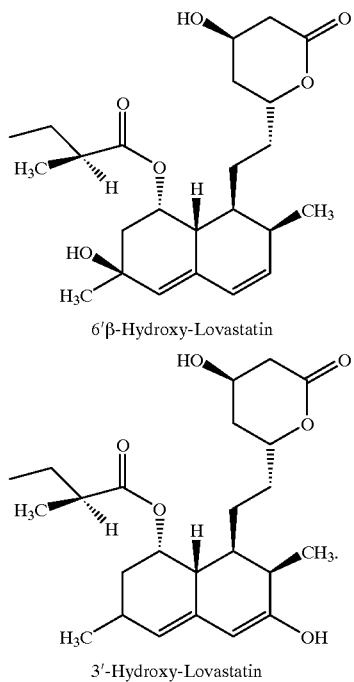

6'β-Hydroxy-Lovastatin

3'-Hydroxy-Lovastatin

BRIEF DESCRIPTION OF THE FIGS.

FIG. 1. Structural formulas of atorvastatin and its hydroxylated metabolites.

FIG. 2. Structural formulas of gemfibrozil and its hydroxylated metabolite.

FIG. 3. The effect of atorvastatin and its hydroxylated metabolites on LDL oxidation in the copper ion oxidative system (A), the AAPH oxidative system (B), and the J-774 A.1 macrophage oxidative system (C). LDL (100 μg of protein/mL) was incubated in all three oxidative systems with increasing concentration of the drug or its metabolites for 4 hours at 37° C. in systems A and B, and for 20 hours with the cells (C). At the end of the incubation, LDL oxidation was measured by the TBARS assay. Macrophage-mediated oxidation of LDL was calculated by subtraction of the values obtained in the absence of cells from those obtained in the presence of cells. Results are given as the mean±standard deviation (SD) (n=3).

FIG. 4. The effect of atorvastatin and its hydroxylated metabolites on VLDL oxidation in the copper ion oxidative system (A), and in AAPH oxidation system (B). VLDL (100 μg of protein/mL) was incubated with 10 μM of atorvastatin or its metabolites for 4 hours at 37° C. At the end of the incubation, VLDL oxidation was measured by the TBARS assay. Results are given as mean±SD (n=3).

FIG. 5. Free radical scavenging activity (A), and copper ion chelating capability of atorvastatin and its hydroxylated metabolites (B). A. Atorvastatin or its hydroxylated metabolites (20 μM) were incubated with 1 mM DPPH and kinetic determination of the absorbance at 517 nm was performed. A representative experiment out of 3 different studies with similar pattern is shown. Vitamin E (20 μM) was used as a positive control for free radicals scavenger. B. LDL (100 μg of protein/mL) was incubated with atorvastatin or its metabolites (10 μM) and with increasing concentrations of $CuSO_4$ for 4 hours at 37° C., prior, to analysis of lipoprotein oxidation by the TBARS assay. Results are given as mean±SD (n=3).

FIG. 6. Effect of gemfibrozil and gemfibrozil metabolite concentration on LDL oxidation in the copper ion oxidative system (A), the AAPH oxidative system (B), and J-774 A.1 macrophage oxidative system (C). LDL (100 μg of protein/mL) was incubated in all three oxidative systems with increasing concentrations of the drug or its metabolite, for 4 hours at 37° C. in systems A and B, and for 20 hours with the cells (C). At the end of the incubation, LDL oxidation was measured by the TBARS assay. Macrophage-mediated oxidation of LDL was calculated by subtracting the values obtained in the absence of cells from those obtained in the presence of cells. Results are given as the mean±SD (n=3).

Figure 7A:
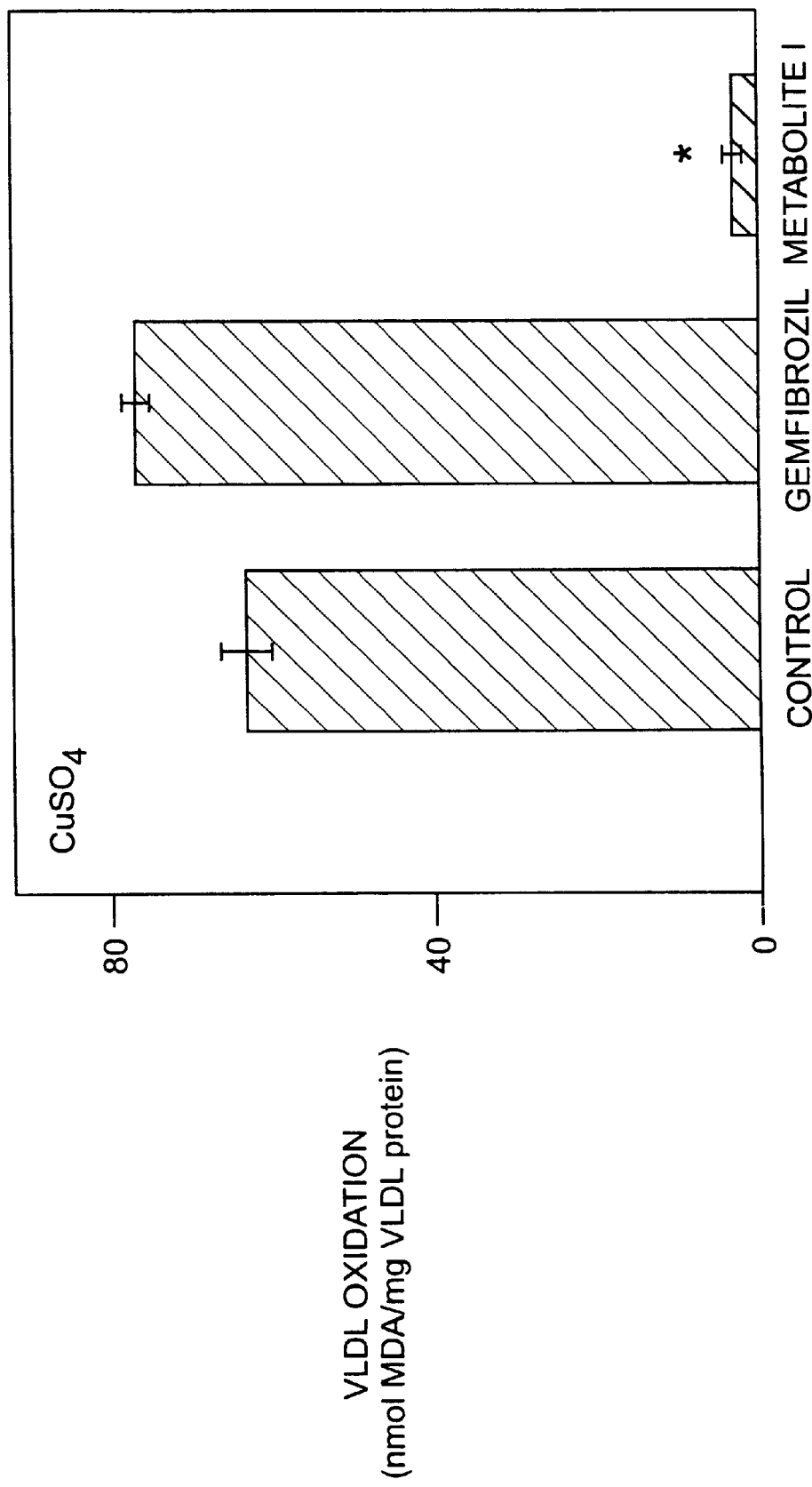

FIG. 7. The effect of gemfibrozil and its metabolite on VLDL oxidation in copper ion oxidative system (A) and in the AAPH oxidation system (B). VLDL (100 μg of protein/mL) was incubated with 4 μM of gemfibrozil or its metabolite for 4 hours at 37° C. At the end of the incubation, VLDL oxidation was measured by the TBARS assay. Results are given as mean±SD (n=3).

Figure 8:
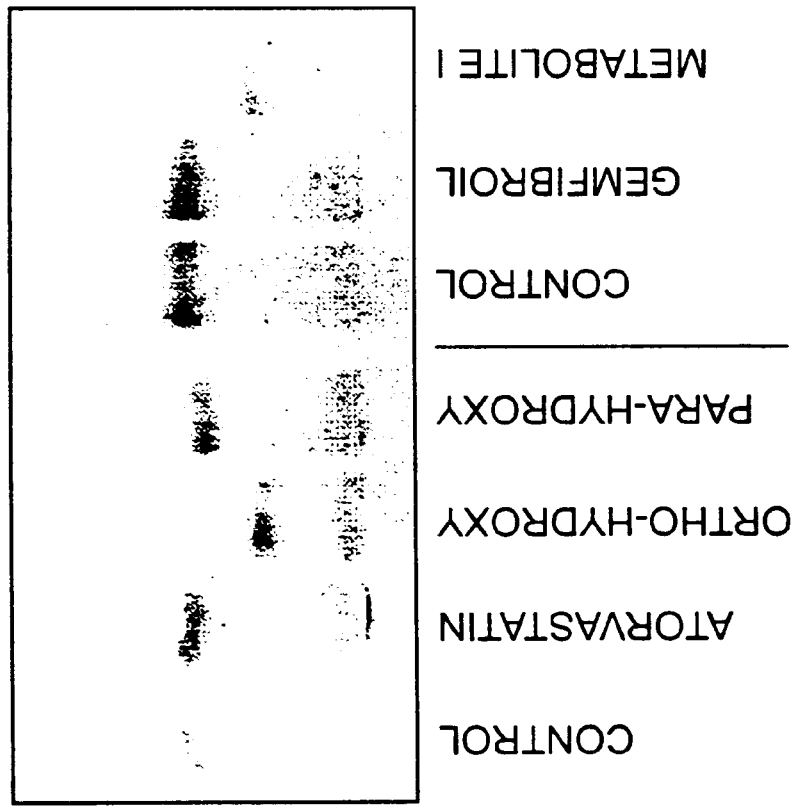

FIG. 8. Lipoprotein electrophoresis of VLDL following copper ions (10 μM $CuSO_4$)-induced lipoprotein oxidation in the absence or presence of atorvastatin, gemfibrozil, or their metabolites.

FIG. 9. Free radical scavenging activity (A), and copper ion chelating capability of gemfibrozil and its metabolite (B). A. Gemfibrozil or its metabolite (20 μM) were incubated with 1 mM DPPH and kinetic determination of the absorbance at 517 mm was performed. A representative experiment out of 3 different studies with similar pattern is shown. Vitamin E (Vit E) at similar concentration was used as a control free radical scavenger. B. LDL (100 μg of protein/mL) was incubated with gemfibrozil or its metabolite (3 μM) and with increasing concentrations of $CuSO_4$ for 4 hours at 37° C. prior to analysis of lipoprotein oxidation by the TBARS assay. Results are given as mean±SD (n=3).

Figure 10:
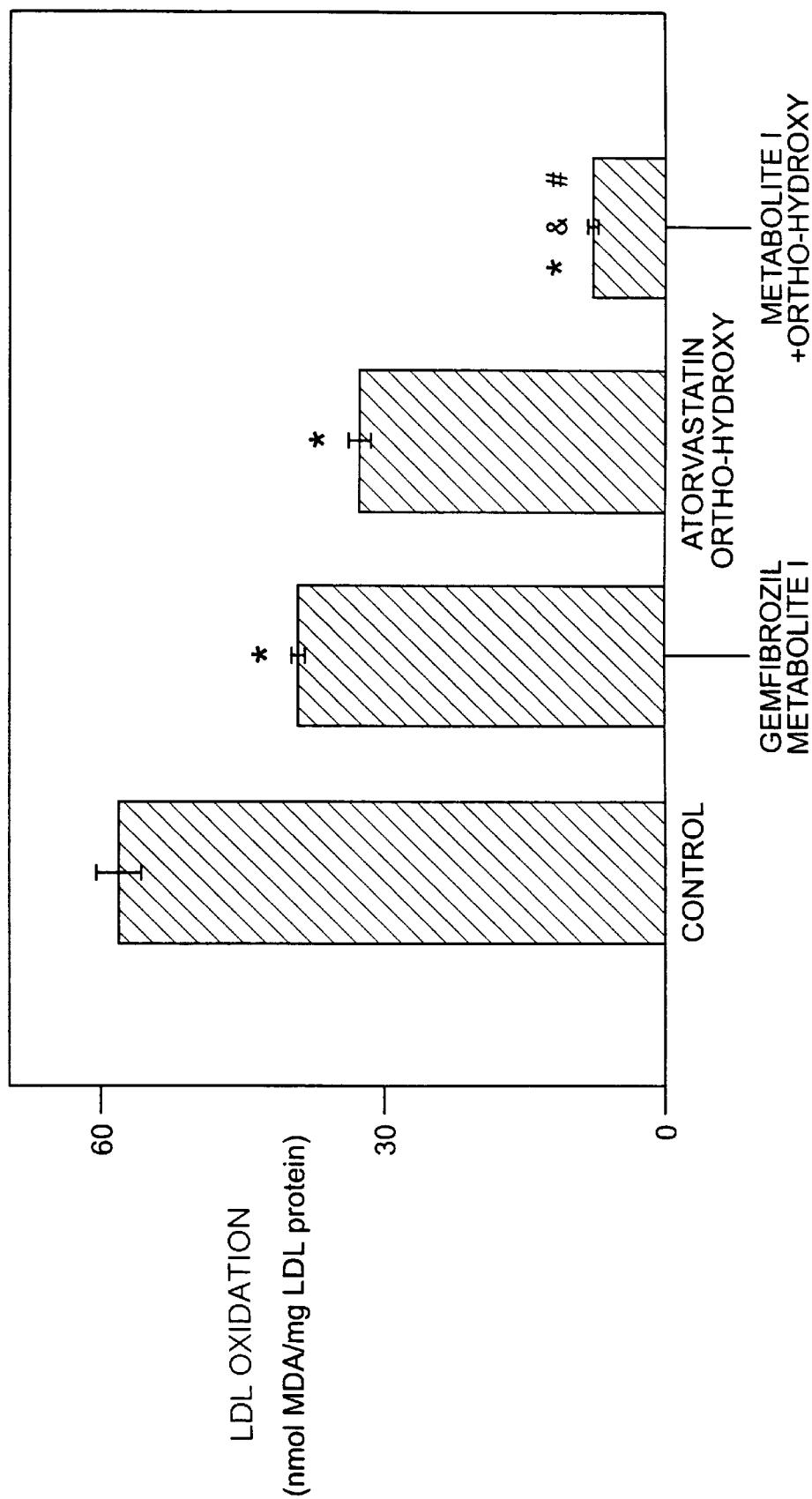

FIG. 10. The combined effect of metabolite I of gemfibrozil and the ortho-hydroxy metabolite of atorvastatin on LDL oxidation. LDL (100 μg of protein/mL) was incubated with 10 μM $CuSO_4$ for 4 hours at 37° C. alone (Control) or in the presence of gemfibrozil metabolite I (3 μM), or the atorvastatin ortho-hydroxy metabolite (4 μM) alone, or in combination. Lipoprotein oxidation was then measured by the TBARS assay. *p<0.01 (vs. Control) and p<0.01 (vs. Metabolite I), #P<0.01 (vs. Ortho-Hydroxy). Results are given as the mean±SD (n=3).

FIG. 11. The dose-dependent antioxidant effects of atorvastatin para-hydroxy metabolite in membrane preparations enriched with polyunsaturated fatty acids.

FIG. 12. The comparative antioxidant potency of atorvastatin para-hydroxy metabolite, Vitamin E, and probucol.

FIG. 13. The antioxidant potency of atorvastatin para-hydroxy metabolite and Vitamin e under atherosclerotic-like conditions of elevated membrane cholesterol.

DETAILED DESCRIPTION OF THE INVENTION

The term "hydroxylated cholesterol lowering agent" means any chemical compound that is effective at lowering LDL cholesterol in a mammal that has at least one hydroxy group substituted on the parent structure, and has antioxidant activity. Examples include hydroxylated statins. The statins are a known class of HMG-CoA reductase inhibitors, such as atorvastatin, fluvastatin, and cerivastatin. Hydroxylated statins are the parent statin compound having at least one hydroxy substituent group, examples being ortho-hydroxy atorvastatin and para-hydroxy atorvastatin as shown in FIG. 1. Other hydroxylated cholesterol lowering agents are hydroxy substituted fibrates, such as hydroxylated gemfibrozil as shown in FIG. 2 (metabolite I). The hydroxylated compound to be used in the method of this invention is preferably a compound having a hydroxy group attached to a phenyl ring.

Increased atherosclerosis risk in hyperlipidemic patients results from enhanced oxidizability of their plasma lipoproteins. While hypocholesterolemic drug therapy, including the 3-hydroxy-3-methyl-glutaryl Coenzyme A (HMG-CoA) reductase inhibitors such as atorvastatin, and the hypotriglyceridemic drug bezafibrate, reduces the enhanced susceptibility to oxidation of low density lipoprotein (LDL) isolated from hyperlipidernic patients, this antioxidative effect could not be obtained in vitro with these drugs. The following experiments establish the effect of atorvastatin and gemfibrozil, as well as specific hydroxylated metabolites, on the susceptibility of LDL, VLDL, and HDL to oxidation (e.g., lipid peroxidation). Lipid peroxidation, induced by either copper ions (10 $\mu$M $CuSO_4$), by the free radical generator system 2'2'-azobis 2-amidino propane hydrochloride (5 mM AAPH), or by the J-774A.1 macrophage-like cell line, was not inhibited by the parent forms of atorvastatin or gemfibrozil, but was substantially inhibited (by 57%–97%), in a concentration-dependent manner, by pharmacological concentrations of the ortho-hydroxy and the para-hydroxy metabolites of atorvastatin, as well as by para-hydroxy metabolite (metabolite I) of gemfibrozil. On using the atorvastatin ortho-hydroxy metabolite and gemfibrozil metabolite I in combination, an additive inhibitory effect on LDL oxidizability was found. Similar inhibitory effects (37%–96%) of the above metabolites were obtained for the susceptibility of VLDL and HDL to oxidation in the oxidation systems outlined above. The inhibitory effects of these metabolites on LDL, VLDL, and HDL oxidation could be related to their free radical scavenging activity, as well as (mainly for the gemfibrozil metabolite I) to their metal ion chelation capacities. In addition, inhibition of HDL oxidation was associated with preservation of HDL-associated paraoxonase activity. The data establish that atorvastatin hydroxy metabolites, and gemfibrozil metabolite I, possess potent antioxidative potential, and as a result protect LDL, VLDL, and HDL from oxidation. The hydroxylated cholesterol lowering agents thus are useful to reduce the atherogenic potential of lipoproteins through their antioxidant properties.

LDL oxidation is a key process in early atherogenesis and thus, inhibition of LDL oxidation is antiatherogenic. VLDL and HDL oxidation also occurs during oxidative stress and also contributes to atherogenesis. Antioxidants are derived environmentally as well as genetically. For example, dietary antioxidants, such as vitamin E, carotenoids, or polyphenolic flavonoids, associated with lipoproteins, protects them from oxidation. In addition, genetic factors, such as HDL-associated paraoxonase, also protects this lipoprotein from the damage of oxidative stress. The enhanced susceptibility of LDL to oxidation derived from hypercholesterolemic patients is significantly reduced by hypocholesterolemic therapy. Thus, hypolipidemic therapy may be considered beneficial not only because of its effects on plasma VLDL, LDL, and HDL levels, but also since it can reduce the formation of atherogenic oxidized lipoproteins.

The ex vivo inhibition of LDL oxidation has been shown following the administration of the HMG-CoA reductase inhibitors lovastatin, simvastatin, pravastatin, or fluvastatin to hypercholesterolemic patients. The inhibitory effect of these drugs on LDL oxidizability was suggested to result from enhanced removal of plasma "aged LDL", which is more prone to oxidation than newly synthesized LDL. This effect would be secondary to the statin-induced stimulation of LDL receptor activity in liver cells and to inhibition of hepatic VLDL and LDL production. Metabolites of the parent statins, which are produced in the liver during drug therapy, may also be involved mechanistically. The hepatic P450 drug metabolizing system activity participates in altering the parent statin structure, usually by hydroxylation. Indeed, all the above statins, with the exception of fluvastatin, did not demonstrate direct antioxidant effects on in vitro LDL oxidation when tested at concentrations comparable to the blood drug levels observed in treated hypercholesterolemic subjects. Atorvastatin, a new inhibitor of HMG-CoA-reductase, is the most effective statin for reducing both plasma total and LDL cholesterol levels. This compound also possesses significant hypotriglyceridemic properties towards all lipoprotein fractions. Atorvastatin therapy increases LDL receptor activity and inhibits direct production of apolipoprotein B-100 containing lipoproteins. Both parent drug and its metabolites have relatively long circulation half lives of 14 to 36 hours. Fibrate drugs may also affect the susceptibility of lipoproteins to oxidation; for example, bezafibrate possesses such a capability. The fibric acid derivatives are lipid regulating drugs that promote the catabolism of triglyceride-rich lipoproteins, secondary to the activation of lipoprotein lipase, and to the reduction of apoC-III synthesis. Another fibrate, gemfibrozil has been shown to not only reduce plasma triglycerides, but also to increase plasma HDL concentration in humans and to reduce plasma lipoprotein (a) levels in male cynomolgus monkeys. In humans, gemfibrozil is metabolized to gemfibrozil acyl glucuronides, and these metabolites are found in the plasma and urine of volunteers following treatment. The level of the para-hydroxy metabolite of gemfibrozil (metabolite I) found in the plasma of gemfibrozil-treated rodents is much higher than that of treated humans and likely reflects differences in dose and metabolism. We have now shown the effects of atorvastatin and gemfibrozil, as well as specific hydroxylated metabolites (alone and in combination) on LDL, VLDL, and HDL susceptibility to oxidation. The results clearly demonstrate inhibitory effects of the drug metabolites (but not of the parent drugs) on plasma lipoprotein oxidation individually, and an additive effect, when combined. The data establish that the hydroxylated derivatives are useful to prevent lipoprotein oxidation and thereby reduce their atherogenic potential.

The following detailed examples demonstrate the antioxidant activity of various hydroxylated cholesterol lowering agents.

EXAMPLE 1

Materials—Atorvastatin and its ortho-hydroxy and para-hydroxy metabolites (FIG. 1), as well as gemfibrozil and its metabolite I (FIG. 2) were synthesized by prior art methods. 2,2-Azobis 2-amidinopropane hydrochloride (AAPH) was purchased from Wako Chemical Industries, Ltd. (Osaka, Japan). 1,1-Diphenyl-2 picryl-hydrazyl (DPPH) was purchased from Sigma (St. Louis, Mo.).

Lipoproteins—Serum VLDL, LDL, and HDL were isolated from fasted normolipidemic volunteers. Lipoproteins were prepared by discontinuous density gradient ultracentrifugation. The lipoproteins were washed at their appropriate densities (1.006 g/mL, 1.063 g/mL, and 1.210 g/mL, respectively), and dialyzed against 150 mM NaCl, (pH 7.4) at 4° C. The lipoproteins were then sterilized by filtration (0.45 $\mu$M), kept under nitrogen in the dark at 4° C., and used within 2 weeks. Prior to the oxidation studies, the lipoproteins were dialyzed against PBS, EDTA-free solution, pH 7.4 under nitrogen at 4° C. The lipoproteins were found to be free of lipopolysaccharide (LPS) contamination when analyzed by the Limulus Amebocyte Lysate assay (Associated of Cape Cod, Inc; Woods Hole, Mass., USA). The lipoprotein protein content was determined by standard methods.

Lipoprotein oxidation—Lipoproteins (100 $\mu$g of protein/mL) were incubated with 10 $\mu$M $CuSO_4$ or with 5 mM of AAPH for 4 hours at 37° C. AAPH is a water-soluble azo compound that thermally decomposes and generates water soluble peroxyl radicals at a constant rate. Oxidation was terminated by the addition of 10 $\mu$M of butylated hydroxy-toluene (BHT) and refrigeration at 4° C. The extent of lipoprotein oxidation was measured by the thiobarbituric acid reactive substances (TBARS) assay, using malodialdehyde (MDA) for the standard curve. In addition, lipoprotein oxidation was also determined by the lipid peroxidation test that analyze lipid peroxides by their capacity to convert iodide to iodine which can be measured photometrically at 365 nm. The kinetics of LDL oxidation was continuously monitored by measuring the formation of conjugated dienes as the increase in the absorbance at 234 nm.

LDL oxidation by macrophages—J-774 A.1 murine macrophages-like cell line was purchased from the American Type Culture Collection (Rockville, Md.). The macrophages were grown in Dulbecco's Modified Eagles Medium (DMEM) supplemented with 5% heat inactivated fetal calf serum (FCS). For the lipoprotein oxidation studies, cells ($1\times10^6$/35 mm dish) were incubated with LDL (100 $\mu$g of protein/mL) in RPMI medium (without phenol red) in the presence of 2 $\mu$M $CuSO_4$ for 20 hours at 37° C. in the incubator. Control LDL was also incubated in a cell-free system under the same conditions. At the end of the incubation period, the extent of LDL oxidation was measured in the medium (after centrifugation at 1000×g for 10 minutes) by the TBARS assay. Cell-mediated oxidation of LDL was calculated by subtracting the values obtained in the cell-free system from those obtained with the cells.

Lipoprotein electrophoresis—Lipoproteins (100 $\mu$g protein/mL) were incubated without or with the drugs followed by oxidation in the presence of 10 $\mu$M $CuSO_4$. Then, electrophoresis of the lipoproteins was performed on 1% agarose using a Hydragel-Lipo kit (Sebia, France).

Free radical scavenging capacity—The free radical scavenging capacities of the drugs were analyzed by the 1,1-diphenyl-2-picryl-hydrazyl (DPPH) assay. Each drug (20 $\mu$M) was mixed with 3 mL of 0.1 nmol DPPH/1 (in ethanol). The time course of the change in the optical density at 517 nm was then kinetically monitored.

Paraoxonase activity measurements—The rate of hydrolysis of paraoxon was assessed by measuring the formation of p-nitrophenol at 412 nm at 25° C. The basal assay mixture included 1.0 mM paraoxon and 1.0 mM $CaCl_2$ in 50 mM glycine/NaOH pH 10.5. One unit of paraoxonase activity produces 1 nmol of p-nitrophenol per minute.

Statistical analyses—The Student t-test was used in comparing two means, whereas analysis of variance (ANOVA) was used when more than two groups were compared. Data are presented as mean±standard deviation (SD).

RESULTS

The effect of atorvastatin and its hydroxy metabolites, as well as that of gemfibrozil and its metabolite, on the susceptibility of lipoproteins to oxidation was studied in several oxidation systems including those containing metal ions (10 $\mu$M $CuSO_4$), those have the capacity to generate free radicals (5 mM AAPH), and those that mimic biological oxidation (J-774A.1 macrophage-like cell line).

Figure 3B:
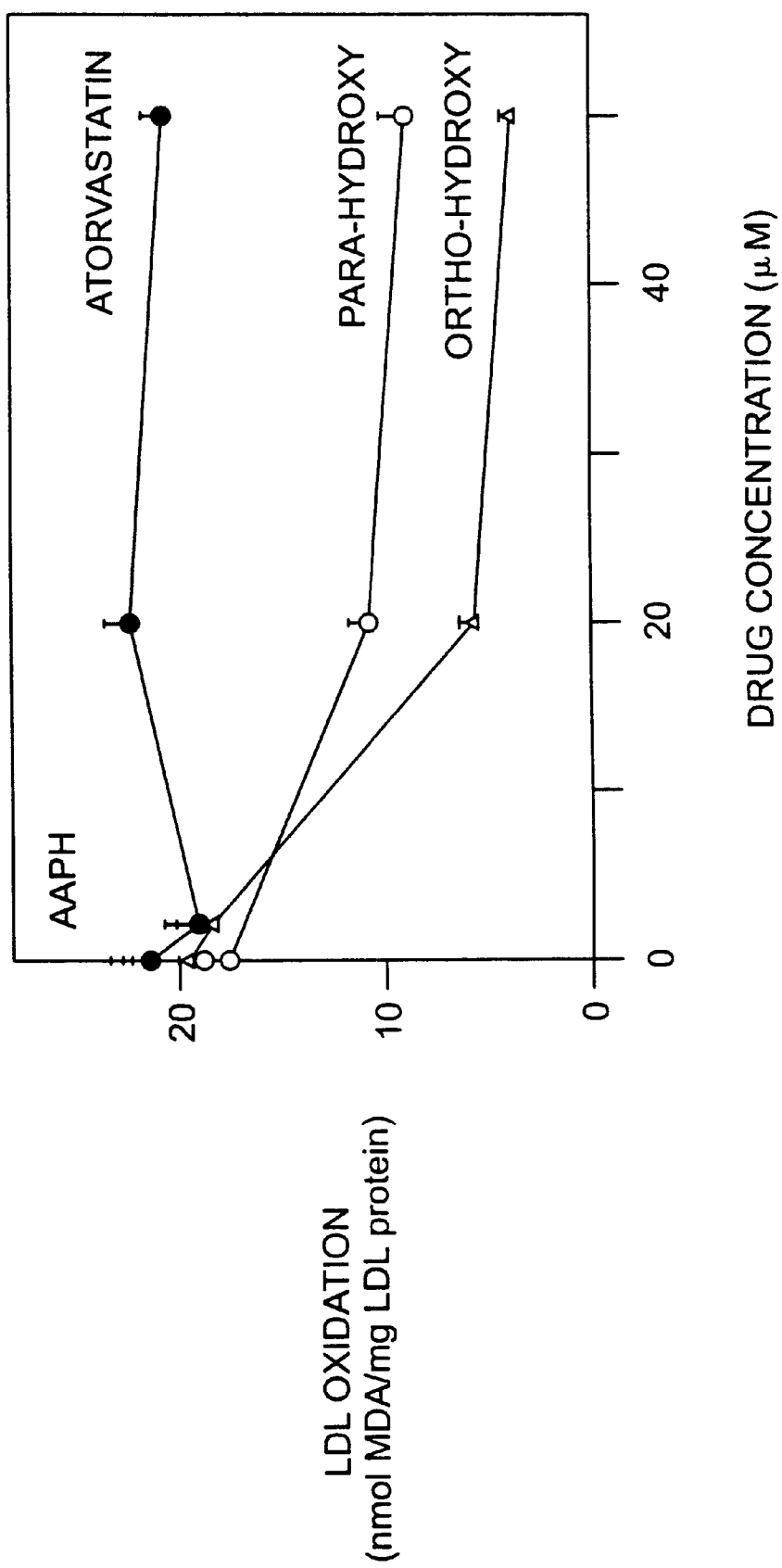
Figure 3C:
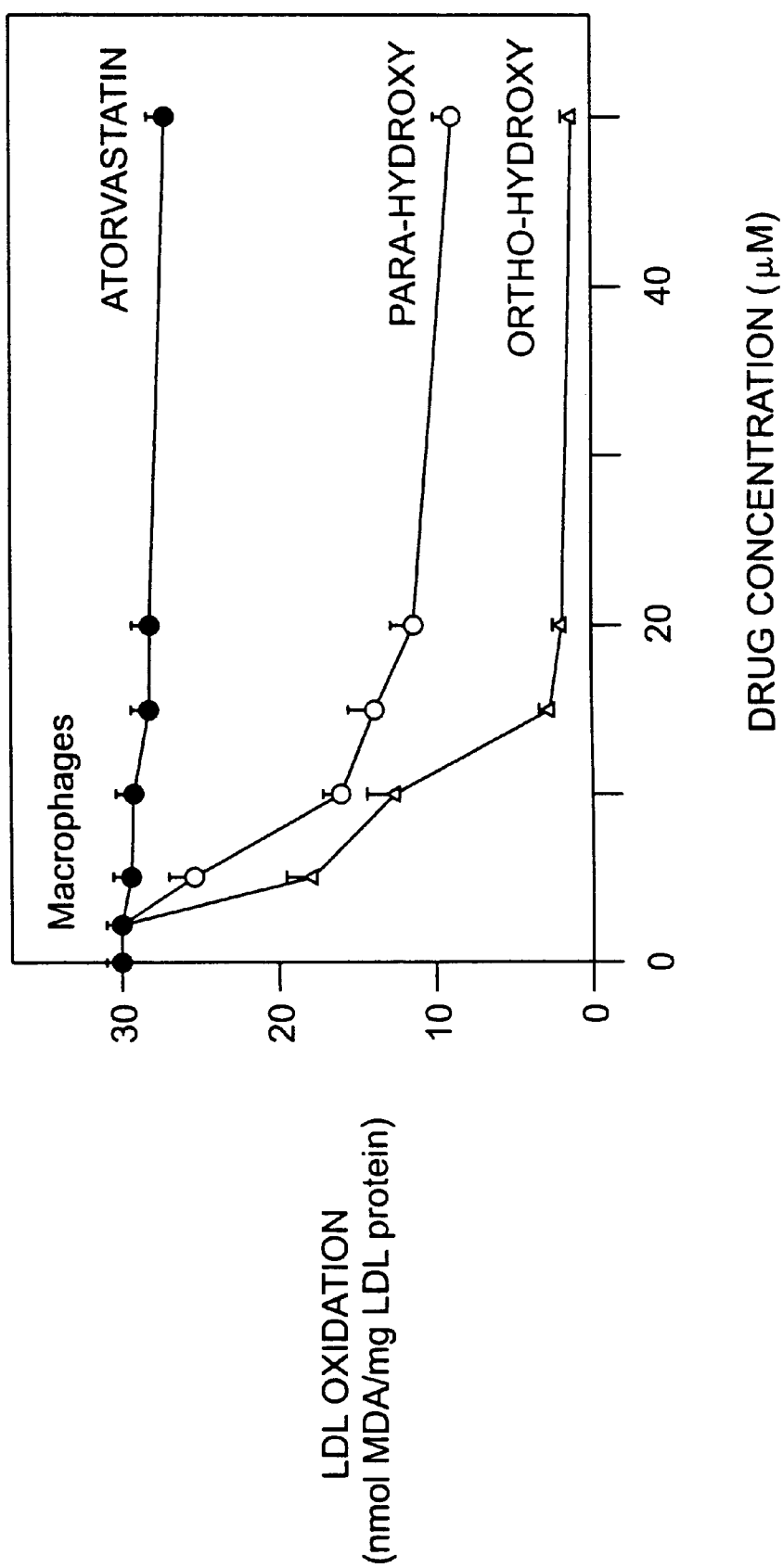

Atorvastatin and lipoprotein oxidation—LDL oxidation was inhibited by the ortho-hydroxy and para-hydroxy atorvastatin metabolites, but not by atorvastatin in all oxidative systems studied. These inhibitory effects were concentration-dependent (FIG. 3). At 10 $\mu$M, both the ortho-hydroxy and the para-hydroxy metabolites inhibited LDL oxidation measured by the TBARS assay in the $CuSO_4$ system by 73% and 60%, respectively (FIG. 3A); in the AAPH system, by 44% and 34%, respectively (FIG. 3B); and in the macrophage system by 50% and 46%, respectively (FIG. 3C). At all concentrations studied and in all oxidation systems, the ortho-hydroxy metabolite was a better LDL oxidation inhibitor than the para-hydroxy metabolite (FIG. 3). A more potent inhibitory effect of both atorvastatin metabolites was obtained in the metal ion oxidation system (FIG. 3A), in comparison to that induced by the free radical generating system (FIG. 3B). Similar results were obtained in the other oxidative systems when LDL oxidation was determined by analyses of lipoprotein-associated peroxides. The ortho-hydroxy and para-hydroxy metabolites of atorvastatin reduced LDL-associated peroxides content from 710±51 in control LDL, to 192±15 and 284±13 nmol/mg LDL protein in the $CuSO_4$ system, respectively, and from 990±89 in control LDL, to 554±32 and 624±38 nmol/mg LDL protein in the AAPH system, respectively. Furthermore, kinetic analysis of conjugated dienes formations at 234 nm during copper ion (10 $\mu$M $CuSO_4$)-induced LDL oxidation, revealed that the lag time required for the initiation of LDL oxidation was 50±7 minutes (n=3) for either control or atorvastatin-treated LDL, whereas LDL conjugated dienes formation initiated only after 180±25 minutes (n=3) for both of the atorvastatin metabolites.

Figure 4A:
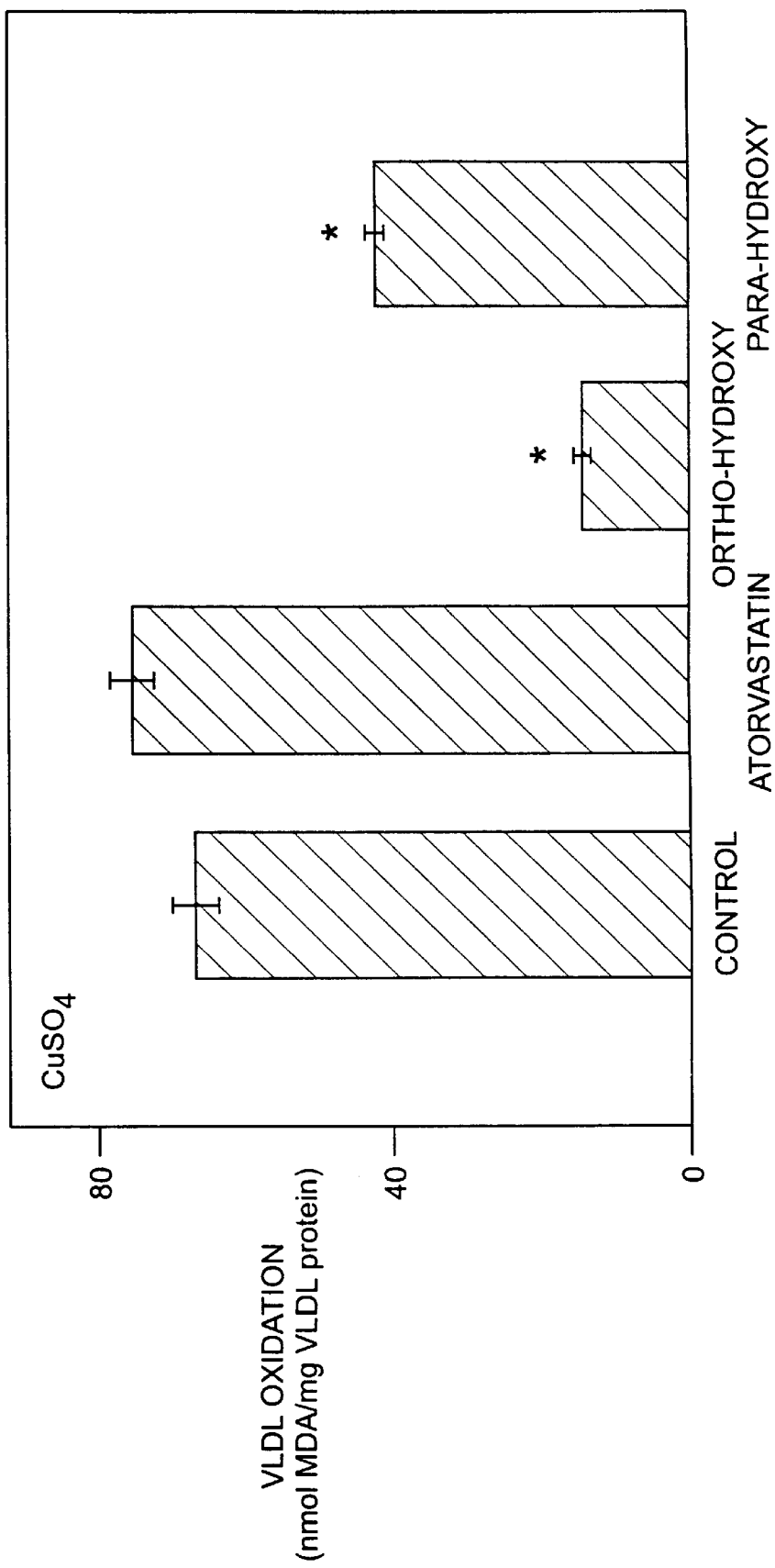
Figure 4B:
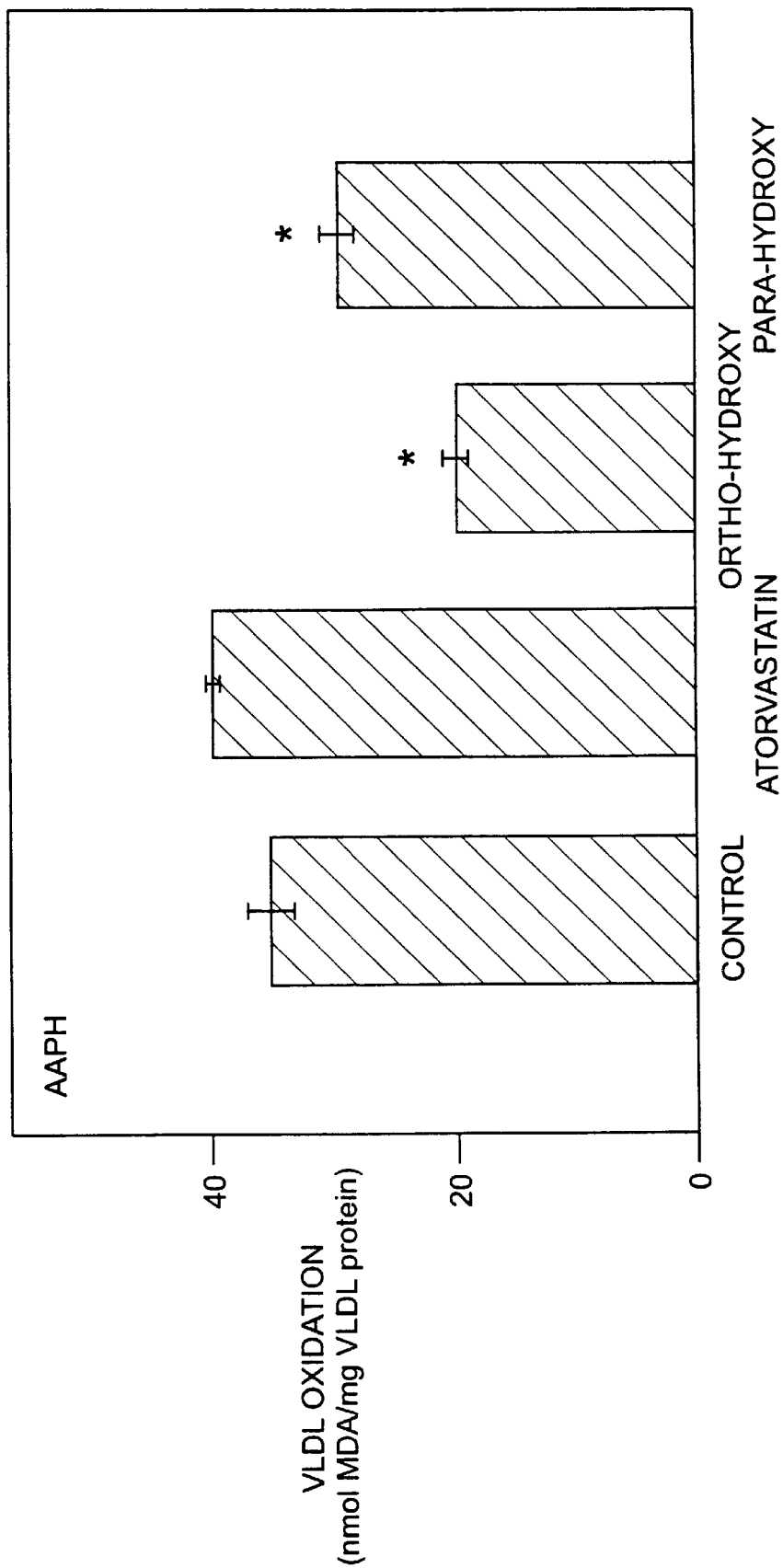

The effect of atorvastatin and its metabolites on VLDL oxidation is reported in FIG. 4. In the copper ion oxidative system, the ortho-hydroxy and para-hydroxy metabolites (10 $\mu$M) inhibited lipoprotein oxidation by 79% and 37%, respectively (FIG. 4A), whereas atorvastatin itself had no effect. In the AAPH oxidative system, the inhibitory effects of these metabolites were only 43% and 16%, respectively FIG. 4B), and again atorvastatin itself had no effect. Similar results were found when VLDL oxidation was analyzed by peroxide formation. The ortho-hydroxy and the para-hydroxy metabolites of atorvastatin reduced VLDL-associated peroxide content from 1818±333 in control VLDL, to 242±22 and 1088±310 nmol/mg VLDL protein in the $CuSO_4$ system, respectively, and from 2169±329 in control VLDL, to 1228±210 and 1819±228 nmol VLDL protein in the AAPH system, respectively. Similarly, HDL oxidation in the presence of $CuSO_4$ under similar incubation conditions revealed that the ortho-hydroxy metabolite completely inhibited HDL oxidation, whereas the para-hydroxy metabolite inhibited the lipoprotein oxidation by about 50% (Table 1). The inhibitory effects of these metabolites on HDL oxidation were associated with the protection of paraoxonase by 54% and 27%, respectively. Elevated activities of the HDL-associated paraoxonase were noted, in comparison to paraoxonase activity in HDL that was oxidized in the absence of added parent drug (Table 1).

TABLE 1

The Effect of Atorvastatin and Its Metabolites on HDL Oxidation and on HDL-Associated Paraoxonase Activity

| | $CuSO_4$-Induced HDL Oxidation (nmoL/mg HDL Protein) | | Paraoxonase Specific Activity |
|---|---|---|---|
| | MDA | Peroxides | (nmoL/mg HDL Protein/min) |
| Control | 9.1 ± 0.1 | 122 ± 14 | 26 ± 2 |
| Atorvastatin | 9.6 ± 0.5 | 122 ± 15 | 29 ± 4 |
| Ortho-Hydroxy Metabolite | 0.2 ± 0.1* | 9 ± 1* | 40 ± 4* |
| Para-Hydroxy Metabolite | 4.5 ± 0.3* | 65 ± 9* | 33 ± 3* |

*p < 0.01 (vs. Control)

Figure 5A:
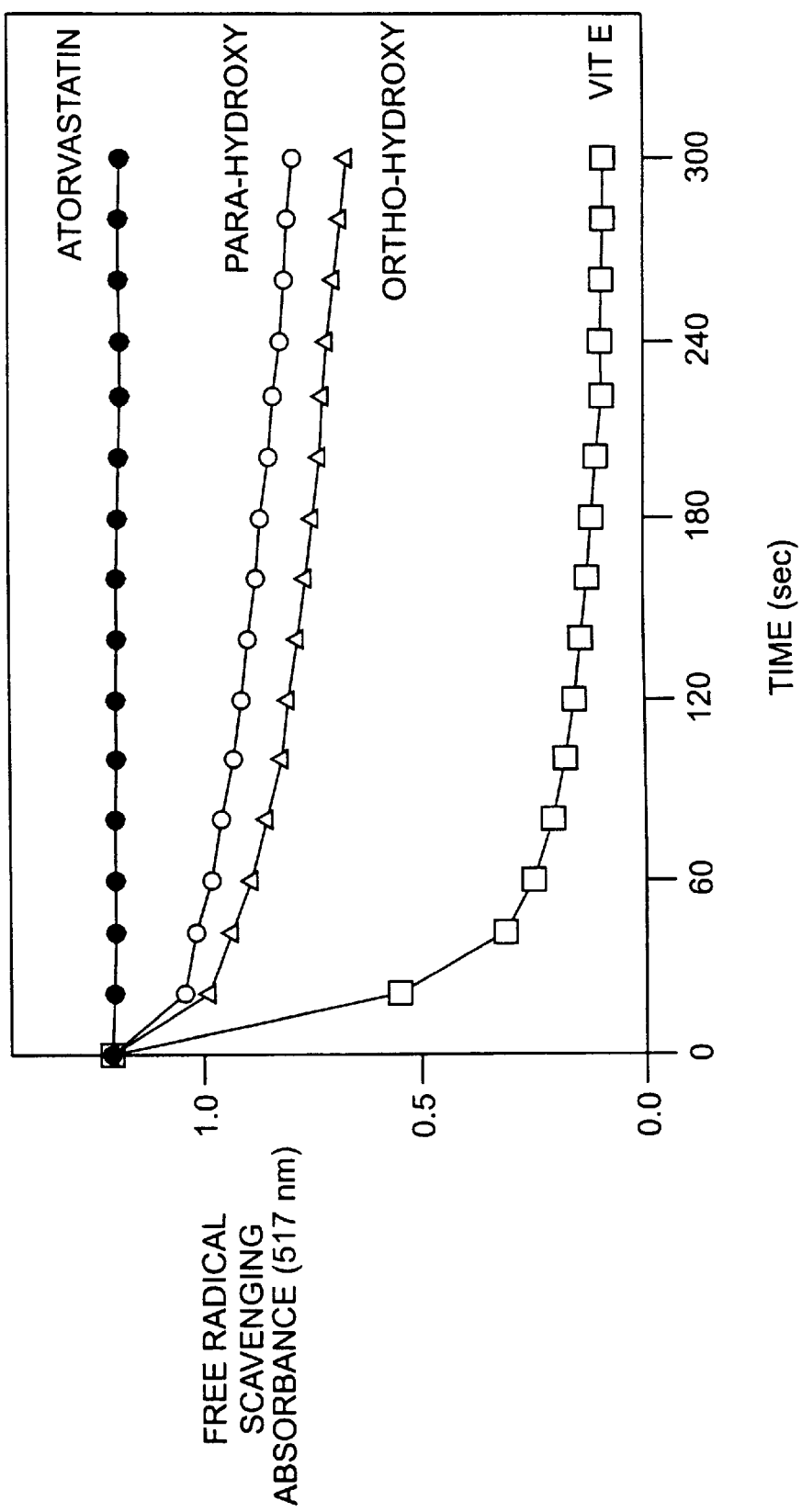

The inhibitory effects of the atorvastatin metabolites on lipoprotein oxidation is also related to a free radical scavenging activity and to a metal ion chelating capability. In the DPPH assay, a time-dependent reduction in the absorbance at 517 nm by both metabolites of atorvastatin (20 $\mu$M), but not by atorvastatin (FIG. 5A) was observed. After 300 seconds of incubation, the ortho-hydroxy and the para-hydroxy metabolites reduced the absorbance at 517 nm by 37% and 28%, respectively. For comparison, a 95% reduction in the absorbance at was obtained by 20 $\mu$M of the free radical scavenger antioxidant, vitamin E (FIG. 5A). These results establish that the atorvastatin metabolites possess substantial free radical scavenging abilities.

Figure 5B:
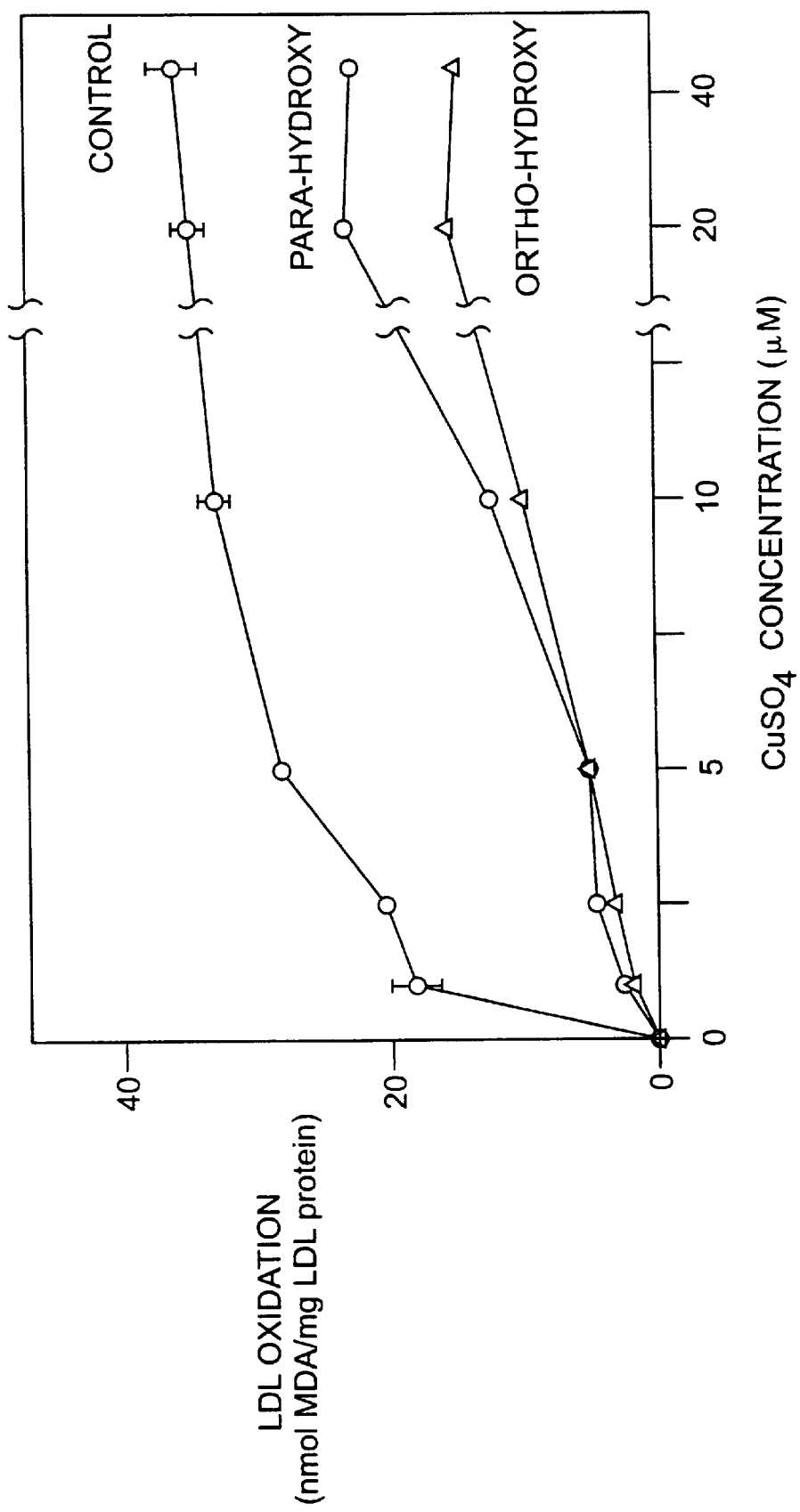

The ability of atorvastatin metabolites to act as inhibitors of LDL oxidation by chelation of copper ions was tested by LDL incubation with increasing concentrations of $CuSO_4$ to 2 hours at 37° C. in order to determine whether excess concentrations of copper ions can overcome the inhibitory effect of these metabolites on LDL oxidation (FIG. 5B). The addition of increasing concentrations of copper ions to the incubation system caused only a minor increase in LDL oxidation when the metabolites were present, in comparison to control LDL (FIG. 5B), indicating only minimal capabilities of these metabolites to inhibit LDL oxidation via chelation of metal ions.

EXAMPLE 2

Gemfibrozil and lipoprotein oxidation

Figure 6A:
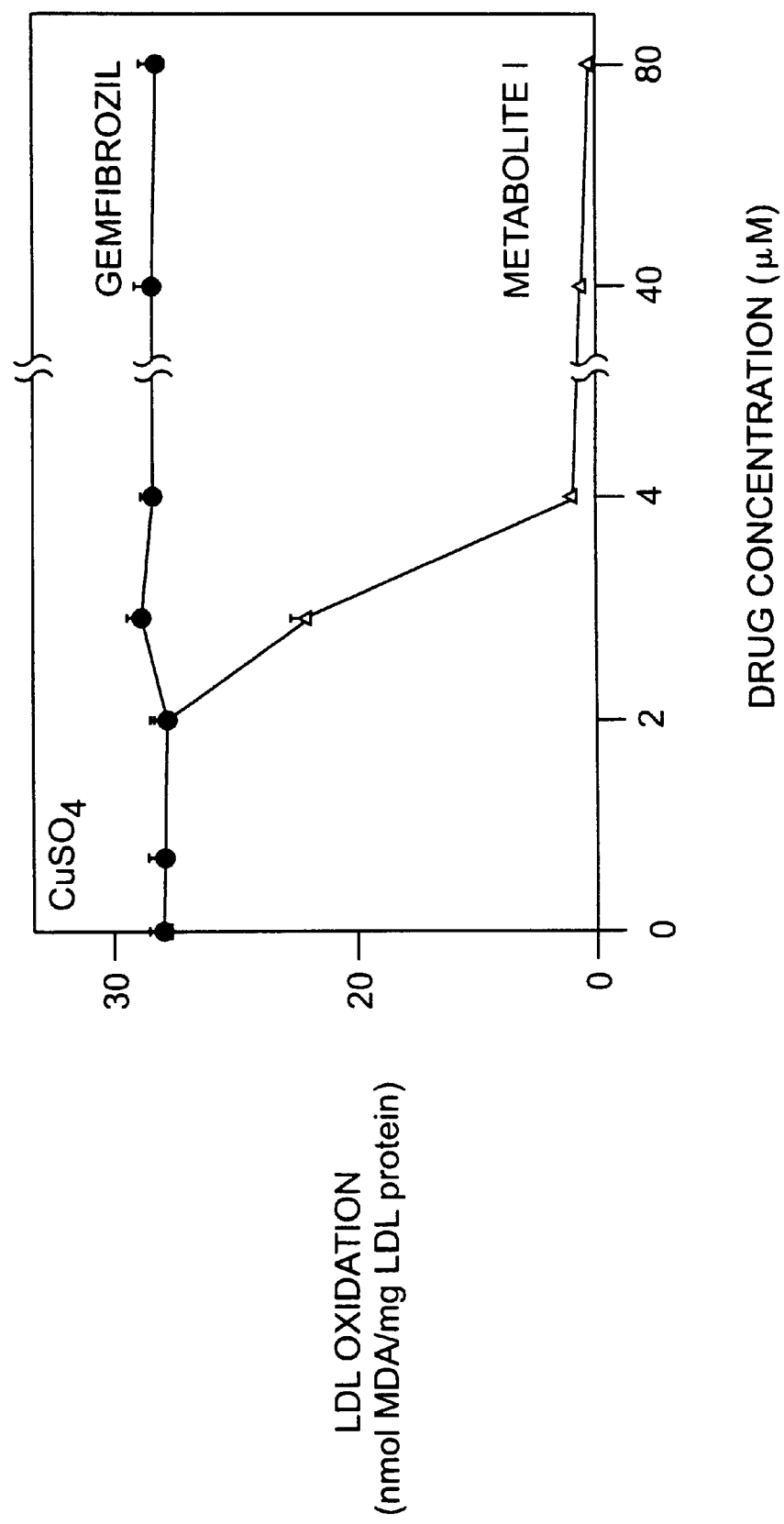
Figure 6B:
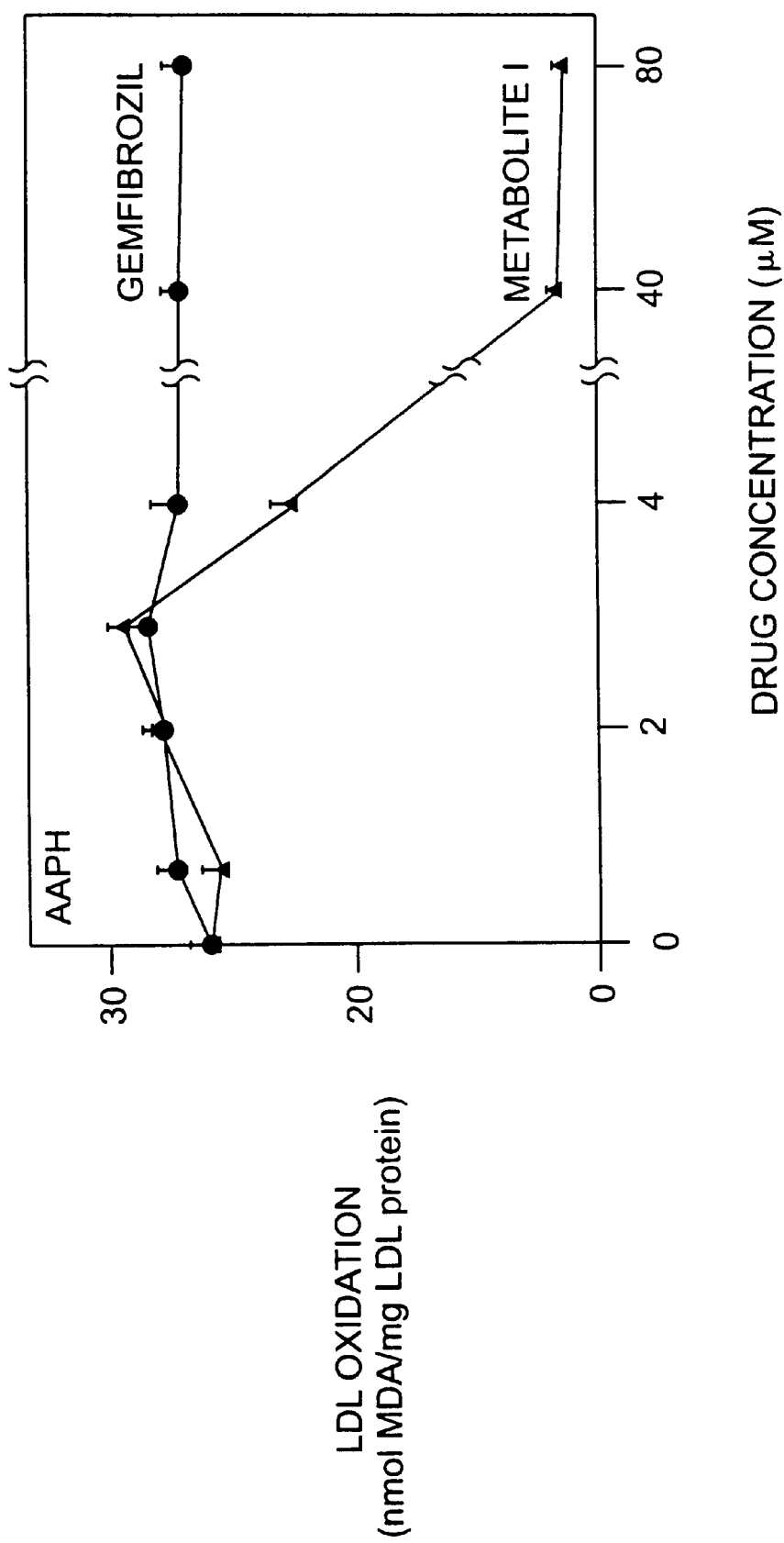
Figure 6C:
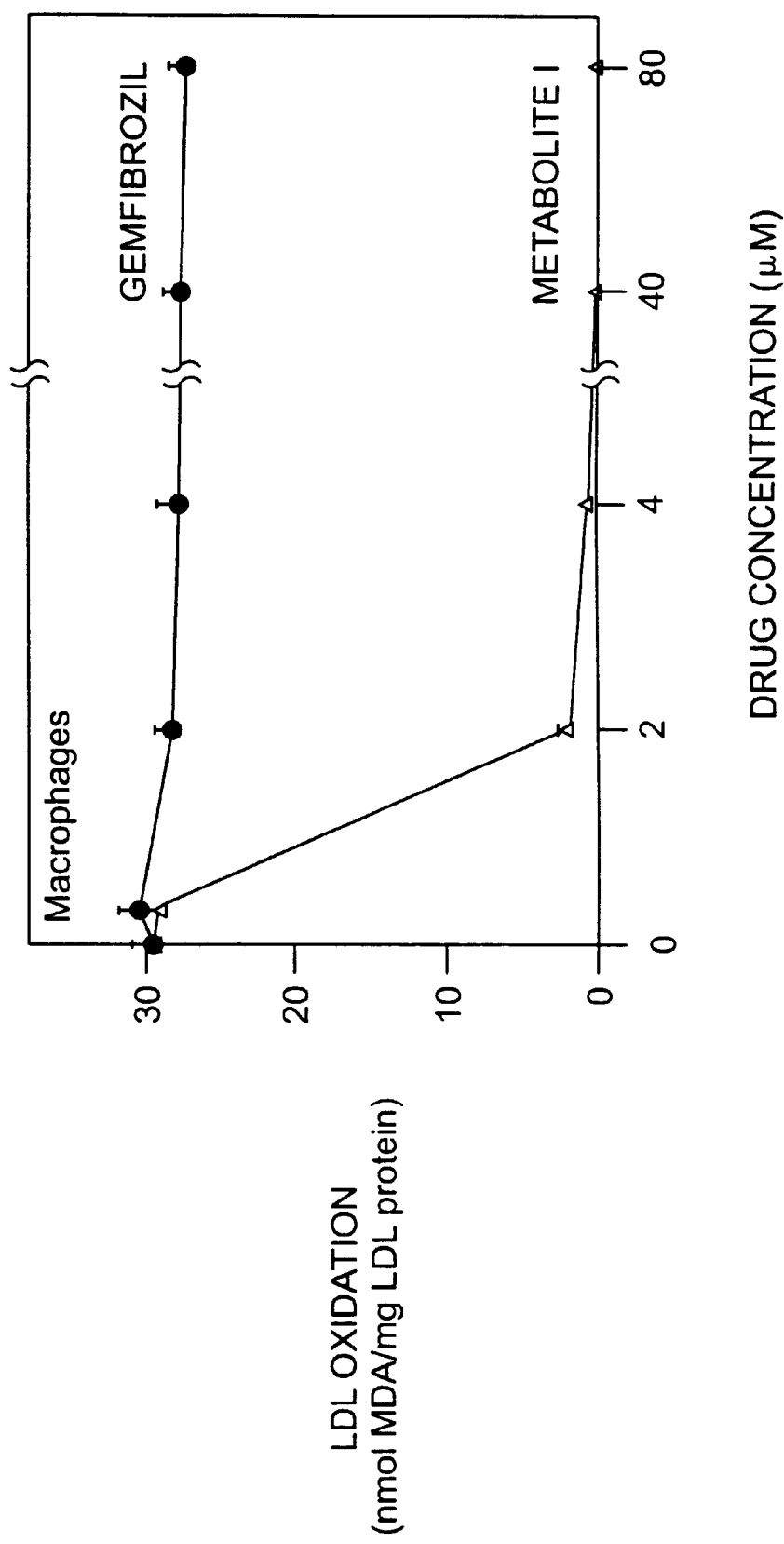

The above experiments were conducted to determine the effects of gemfibrozil and one of its metabolites (metabolite I) on LDL oxidation, and is similar to that shown for atorvastatin (FIGS. 3–5). LDL oxidation was inhibited by metabolite I, but not by gemfibrozil itself, in all studied oxidative systems. This inhibitory effect of metabolite I was concentration-dependent (FIG. 6). At a concentration as low as 4 $\mu$M, gemfibrozil metabolite I inhibited LDL oxidation, measured by the TBARS assay, by 96% in the $CuSO_4$ oxidative system (FIG. 6A), by 26% in the AAPH oxidative system (FIG. 6B), and by 99% in the J-774 A.1 macrophage-mediated oxidation system (FIG. 6C). Similar results were found when LDL oxidation was analyzed by the amount of peroxides formed. The gemfibrozil metabolite I reduced LDL-associated peroxides from 710±57 to 28±7 nmol/mg LDL protein in the $CuSO_4$ system, and from 917±78 to 703±38 nmol/mg LDL protein in the AAPH system. Furthermore, the time required for the initiation of LDL oxidation (measured by kinetic analysis of conjugated dienes formation), revealed a lag time of 60±9 minutes for LDL alone or LDL in the presence of gemfibrozil. In contrast, even after 240 minutes of incubation with gemfibrozil metabolite I, no conjugated diene formation in LDL was observed.

Figure 7B:
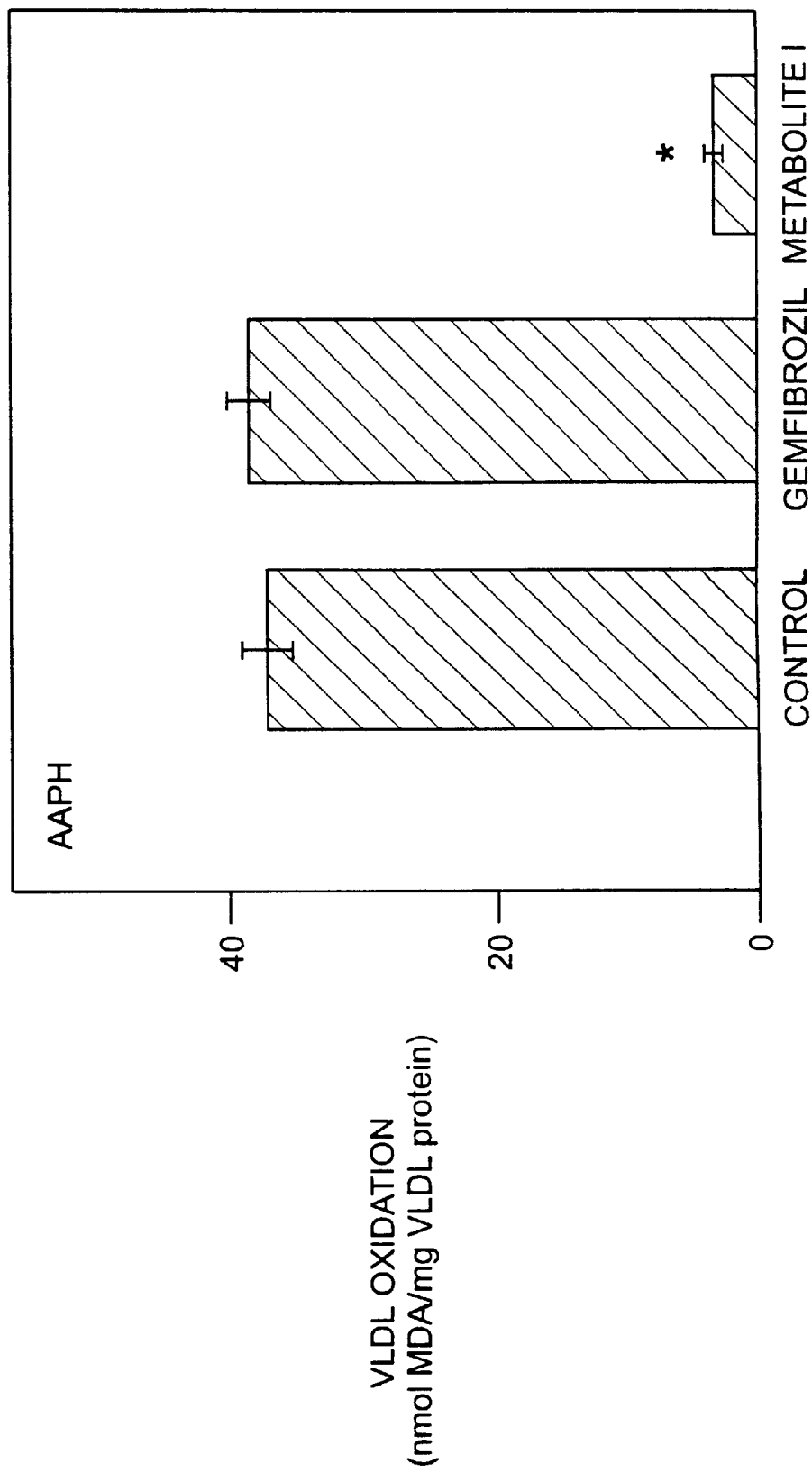

Analyses of the effect of gemfibrozil and its metabolite on VLDL oxidation again showed a very potent inhibitory effect of metabolite I (4 $\mu$M), but not of gemfibrozil, with 96% inhibition of VLDL oxidation in the $CuSO_4$ oxidative system (FIG. 7A) and 91% inhibition in the AAPH oxidative system (FIG. 7B).

Lipoprotein electrophoresis of VLDL, following its oxidation with atorvastatin and its metabolites, or in the presence of gemfibrozil and its metabolite, clearly demonstrated the potency of the atorvastatin ortho-hydroxy metabolite and of gemfibrozil metabolite I to reduce lipoprotein electrophoretic migration (FIG. 8). Similar results were obtained for LDL and for HDL.

Upon oxidation of HDL in the presence of 10 $\mu$M $CuSO_4$, metabolite I of gemfibrozil substantially inhibited lipoprotein oxidation (Table 2), with a concomitant protection of paraoxonase activity, preserving the initial level of HDL-associated paraoxonase activity (Table 2). Gemfibrozil itself had no effect.

Lipoprotein oxidation was carried out for 4 hours at 37° C. with 10 $\mu$M $CuSO_4$, in the absence (Control) or presence of 10 $\mu$M of the drugs. HDL paraoxonase activity before its incubation with the copper ions was 50±3 nmol/mg HDL protein/min. Results are given as the mean±SD (n=3).

TABLE 2

The Effect of Gemfibrozil and Its Metabolites on HDL Oxidation and on HDL-Associated Paraoxonase Activity

| | $CuSO_4$-Induced HDL Oxidation (nmoL/mg HDL Protein) | | Paraoxonase Specific Activity |
|---|---|---|---|
| | MDA | Peroxides | (nmoL/mg HDL Protein/min) |
| Control | 9.1 ± 0.1 | 122 ± 14 | 26 ± 3 |
| Gemfibrozil | 8.2 ± 0.4 | 134 ± 13 | 27 ± 5 |
| Metabolite I | 0.8 ± 0.1* | 18 ± 4* | 50 ± 7* |

*p < 0.01 (vs. Control)

Figure 9A:
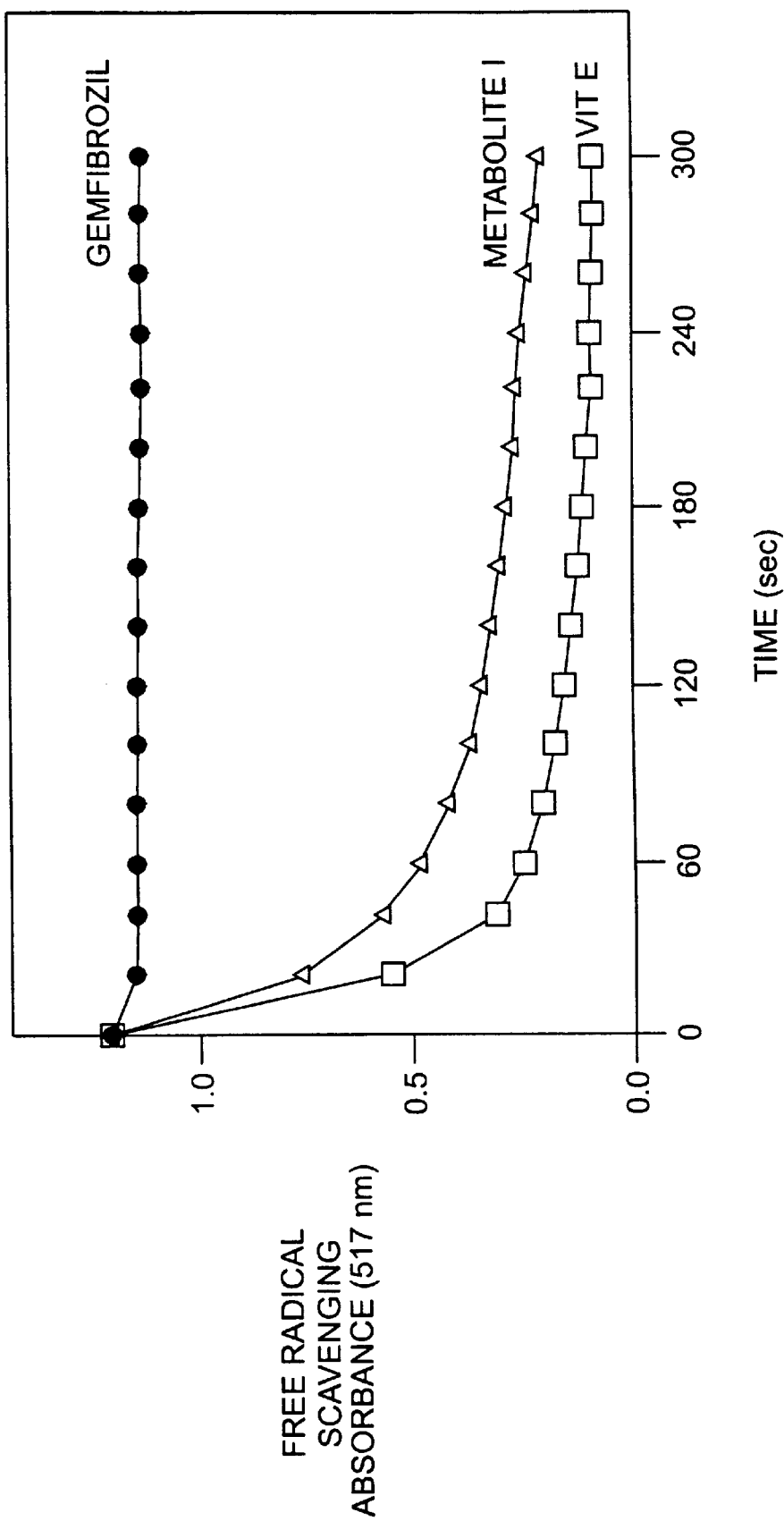
Figure 9B:
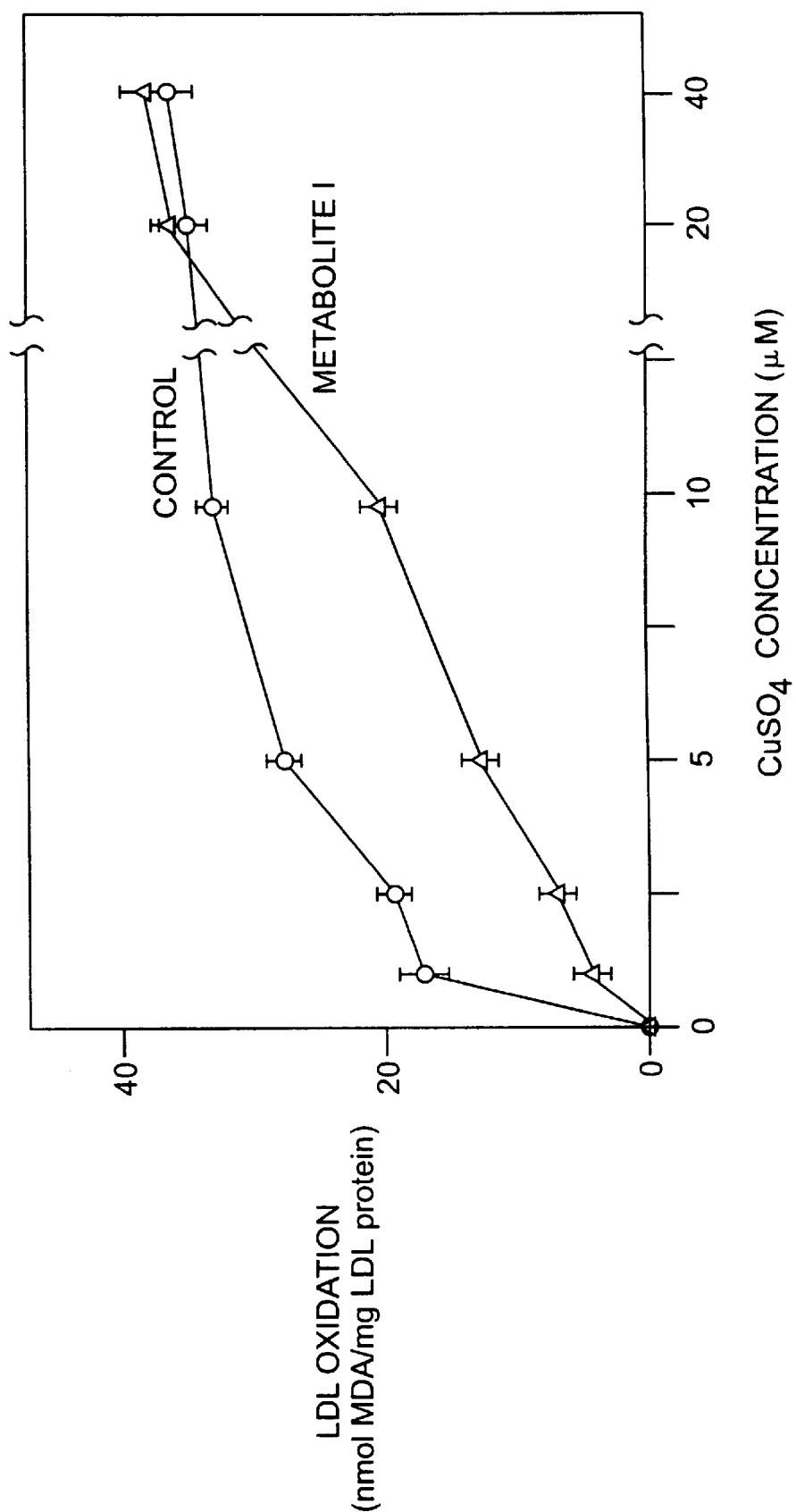

On analyzing the mechanisms responsible for the inhibition of lipoprotein oxidation by gemfibrozil metabolite I, both free radical scavenging ability (FIG. 9A) and copper ion chelation capacity of this metabolite were shown (FIG. 9B). On using the DPPH assay, only metabolite I, but not gemfibrozil itself (20 $\mu$M), demonstrated a time-dependent reduction in the absorbance of 517 nm, with up to 86% reduction in the optical density after 300 seconds of incubation (FIG. 9A). LDL incubation with increasing concentrations of $CuSO_4$ for 2 hours at 37° in the presence of gemfibrozil metabolite I revealed that on using 20 $\mu$M $CuSO_4$, the inhibitory effect of metabolite I was completely prevented (FIG. 9B), indicating that in this LDL oxidation system, chelation of copper ions by metabolite I plays a role in the inhibition of lipoprotein oxidation.

EXAMPLE 3
Interaction Between Atorvastatin and Gemfibrozil

The general procedures described above were repeated to determine whether the in vitro addition of the potent metabolites combined (gemfibrozil metabolite I and atorvastatin ortho-hydroxy metabolite) produces a greater inhibitory effect on LDL oxidation than either agent alone. On using low concentrations of metabolite I of gemfibrozil (3 $\mu$M) or of the ortho-hydroxy metabolite of atorvastatin (4 $\mu$M), only 40% or 43% inhibitory effect of each of these drugs on copper ion-induced LDL oxidation was observed, respectively, in comparison to control LDL (FIG. 10). However, on using a combination of these metabolites at the above concentrations, a significant additive inhibitory effect of 88% was observed for LDL oxidation (FIG. 10).

EXAMPLE 4

Atorvastatin para-hydroxy metabolite, and the known antioxidants Vitamin E and probucol, were evaluated in membrane vesicles enriched with polyunsaturated fatty acids. For the lipid peroxidation experiments, 500 $\mu$L of membrane vesicles were enriched with dilinoleoyl phosphatidylcholine (DLPC) at a concentration of 1.0 mg DLPC/mL. The enriched vesicles were freshly prepared in HEPES buffer (N-(2-hydroxyethyl)piperazine-N'-(2-ethanesulfonic acid) (0.5 mM HEPES, 154.0 mM NaCl, pH 7.3). The buffer solution was prepared without added antioxidant (as a control), and with (1) various concentrations of atorvastatin para-hydroxy metabolite; (2) Vitamin E; and (3) probucol, which is 4,4'-[(1-methyletlmylidene)bid(thio)]bis[2,6-bis(1,1-dimethylethyl)-phenol. The membrane vesicle solutions were immediately placed in a shaking water bath at 37° C. During the incubation period (0–72 hours), 100 $\mu$L aliquot samples were removed and the peroxidation reaction was terminated by adding 25 $\mu$L of 5.0 mM of ethylenediaminetetra acetic acid (EDTA) and 20 $\mu$L of 35.0 mM of butylated hydroxytoluene. The extent of lipid peroxidation in each sample was determined by a spectrophotometric assay for lipid peroxides in serum lipoproteins using a color reagent known as CHOD-iodide (Merck, Darmstadt, FRG, Merck Cat. No. 14106). The color reagent has the following composition:

| | |
|---|---|
| Potassium phosphate, pH 6.2 | 0.2 M |
| Potassium iodide | 0.12 M |
| Sodium azide | 0.15 $\mu$M |
| Polyethyleneglyol mono[p-(1,1',3,3'-tetramethyl-butyl-phenyl] ether | 2 g/L |
| Akylbenzyldimethylammonium chloride | 0.1 g/L |
| Ammonium molybdate | 10 $\mu$M |

The concentration of triiodide formed was measured spectrophotometrically according to the formula (L=lipoprotein)

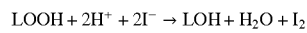

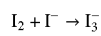

To each of the withdrawn aliquots of membrane vesicles was added 1.0 mL of the CHOD color reagent, and the sample was incubated in the absence of light for 4 hours. The absorbance of the solution was measured at 365 nm ($\epsilon$=2.4× $10^4$ $M^{-1}$ $cm^{-1}$). Lipid peroxide formation was measured in triplicate and values were expressed as mean±SD. The significance of differences between results from different experimental conditions was tested using the two-tailed student t-test.

The antioxidant activity of atorvastatin para-hydroxy metabolite is shown in FIG. 11 for various dose concentrations. The results establish that the para-hydroxy compound has dose-dependent antioxidant activity, and at 10.0 $\mu$M causes 80% inhibition of lipid peroxidation. Even at concentrations as low as 10.0 $\mu$M, the para-hydroxy compound inhibited high levels (>$10^2$ $\mu$M) of lipid peroxidation.

The results shown in FIG. 12 establish that the atorvastatin para-hydroxy metabolite is significantly more active than other known antioxidants, specifically Vitamin E and probucol.

The antioxidant activity of atorvastatin para-hydroxy metabolite increased under atherosclerotic-like conditions of elevated membrane cholesterol, and this is shown in FIG. 13.

The foregoing experiments establish that metabolites of HMG-CoA reductase inhibitors, such as atorvastatin for example, and of fibric acid derivatives, for example gemfibrozil, significantly inhibited lipoprotein oxidation in several oxidation systems. LDL oxidation is a key event in atherogenesis, since it contributes to macrophage cholesterol accumulation and foam cell formation, as well as to cytotoxicity, thrombosis, and inflammation. Hence, inhibition of LDL oxidation contributes to attenuation of the atherosclerotic process. Although not as extensively studied, VLDL and HDL oxidation also occur under oxidative stress, and also facilitates atherosclerosis development. In VLDL, lipid peroxidation mainly involves the oxidation of core triglyceride polyunsaturated fatty acids, whereas in HDL, surface phospholipid fatty acids are the major substrates susceptible to oxidation.

In hypercholesterolemic and in hypertriglyceridemic patients, high blood cholesterol and triglyceride concentrations are risk factors for atherosclerosis. The increased risk is due to enhanced susceptibility of the lipoproteins to oxidation. Several hypolipidemic drugs have been shown to reduce the enhanced propensity of LDL to oxidation in hypercholesterolemic patients. This inhibitory effect on LDL oxidation could result from an enhanced removal (via drug-induced increased LDL receptor activity, mainly in the liver) of "aged LDL" which is more prone to oxidative modifications. In addition, this protective effect against oxidation may result from drug metabolites formed in vivo that possess antioxidant properties. However, with the exception of fluvastatin, none of the parent forms of the studied hypolipidemic drugs demonstrated a direct inhibitory effect on LDL oxidation when tested in vitro at pharmacological concentrations. The above data demonstrates that the parent drugs, atorvastatin and gemfibrozil, do not affect LDL, VLDL, or HDL oxidizability in vitro, even when used at high concentrations. However, low pharmacological concentrations of specific hydroxylated metabolites induce very potent inhibitory effects on LDL, VLDL, and HDL oxidation, both in metal ion-dependent and -independent systems. The drug metabolites inhibitory effect on lipoprotein oxidizability was found to be more pronounced in the $CuSO_4$ system, in comparison to the AAPH system, and this phenomenon may be related to the effects of the metabolites on both scavenging of free radicals and binding of copper ions. Both the gemfibrozil metabolite I and the hydroxy metabolites of atorvastatin were shown to be potent free radical scavengers.

In comparison to the atorvastatin ortho-hydroxy metabolite, gemfibrozil metabolite I acted in the $CuSO_4$ oxidative system as a better metal ion chelator. Increased copper ion concentrations completely abolished the inhibitory effect of gemfibrozil metabolite I, but not that of the atorvastatin metabolites, on LDL oxidation. The molecular structure of the atorvastatin hydroxy metabolites, where the hydroxyl group is attached to the carboxamide portion of the molecule, enable these metabolites to act as electron donors, and hence, as potent antioxidants (FIG. 1). The ortho-hydroxy metabolite is a more potent antioxidant than the para-hydroxy metabolite of atorvastatin, as the hydroxyl group in the ortho position to the amine group (but not the hydroxyl group in the para position), can form a relatively stable transition state of the peroxyl radical, and hence, act as a potent antioxidant. Similarly, in gemfibrozil metabolite I (but not in gemfibrozil), the hydroxyl group on the aromatic ring can substantially contribute to the antioxidative properties of this compound (FIG. 2).

Under oxidative stress, lipoprotein oxidation involves the action of reactive oxygen species, and since transition metal ions are known to be present in areas of the atherosclerotic lesions, the oxidation models used in the above experiments are representative of the in vivo situation.

The inhibitory effects of both the atorvastatin and gemfibrozil metabolites, on LDL oxidation, were also shown for VLDL and HDL. The pattern of inhibition was similar in all studied oxidation systems. These results establish that the metabolites exert their inhibitory effect on lipoprotein oxidation via common mechanisms, i.e., free radical scavenging and metal ion chelation. In one study, in patients with familial combined hyperlipidemia, gemfibrozil therapy did not significantly affect LDL oxidizability. This observation, however, could have resulted from too low a concentration of the drug metabolites to exert an antioxidative effect on LDL oxidation, or the time of sample collection. In addition, drug metabolites could associate with non-lipoprotein components of plasma (e.g. albumin) or be sequestered within cells or interstitial compartments. Thus, the ex vivo examination of oxidation potential of lipoproteins isolated from treated humans or experimental animals may not necessarily reflect the environment of the lipoprotein in vivo.

The data presented above establishes that hydroxylated cholesterol lowering agents inhibit oxidation of lipoproteins by scavenging free radicals and by reducing metal ion chelation of lipoproteins. Accordingly, the invention provides a method for inhibiting lipoprotein oxidation, as well as a method for inhibiting metal ion chelation of lipoproteins, and a method for scavenging free radicals. The amounts of hydroxylated cholesterol lowering agents required to inhibit metal ion chelation of lipoproteins, and to scavenge free radicals, are all referred to herein as an "antioxidant amount".

The hydroxylated cholesterol lowering agents will be administered in an antioxidant amount, namely an amount that is effective to cause an inhibition of lipoprotein oxidation. Such antioxidant effective amounts will be from about 1 to about 100 mg/kg. Such amounts of active agent will be administered from one to about four times a day in order to inhibit lipoprotein oxidation.

The hydroxylated compounds will be formulated for convenient oral or parenteral administration, and will be combined with common excipients and carriers such as calcium carbonate, candelilla wax, hydroxypropyl cellulose, lactose, magnesium stearate, microcrystalline cellulose, polyethylene glycol, talc, and titanium dioxide. For oral administration, the formulations can be pressed into tablets, or encapsulated into gelatin capsules. Typical tablets will contain from about 10 mg of active ingredient to about 80 mg. The compounds can additionally be formulated as slow release dosage forms, for example using osmotic pump technology, as well as transdermal skin patches. For parenteral dosing, the compounds typically are dissolved in isotonic saline for convenient intravenous administration, or for injection.

What is claimed is:

1. A method for inhibiting oxidation of lipoproteins in a mammal comprising administering an antioxidant effective amount of a hydroxylated cholesterol lowering agent selected from a hydroxylated statin or a hydroxylated fibrate.

2. A method of claim 1 employing hydroxylated gemfibrozil, hydroxylated atorvastatin, or hydroxylated fluvastatin.

3. A method of claim 2 employing ortho- or para-hydroxylated atorvastatin.

4. A method for scavenging free radicals in a mammal comprising administering a free radical scavenging amount of a hydroxylated cholesterol lowering agent selected from a hydroxylated statin or a hydroxylated fibrate.

5. A method of claim 4 wherein the hydroxylated cholesterol lowering agent is ortho- or para-hydroxylated atorvastatin, hydroxylated gemfibrozil, or hydroxylated fluvastatin.

6. A method for inhibiting metal ion chelation of lipoproteins in a mammal comprising administering a metal ion chelation inhibiting amount of a hydroxylated cholesterol lowering agent selected from a hydroxylated statin or a hydroxylated fibrate.

7. A method for claim 6 wherein the hydroxylated cholesterol lowering agent is ortho- or para-hydroxylated atorvastatin, hydroxylated gemfibrozil, or hydroxylated fluvastatin.

* * * * *